United States Patent
Shimamoto et al.

(10) Patent No.: US 6,544,736 B1
(45) Date of Patent: Apr. 8, 2003

(54) METHOD FOR SYNTHESIZING CDNA FROM MRNA SAMPLE

(75) Inventors: Akira Shimamoto, Kanagawa (JP); Yasuhiro Furuichi, Kanagawa (JP); Yuko Shibata, Ibaragi (JP); Hiroko Funaki, Toyama (JP); Eiji Ohara, Toyama (JP); Masanori Watahiki, Toyama (JP)

(73) Assignees: Nippon Gene Co., Ltd., Tokyo (JP); Agene Research Institute Co., Ltd., Kamakura (JP)

( * ) Notice: Subject to any disclaimer, the term of this patent is extended or adjusted under 35 U.S.C. 154(b) by 0 days.

(21) Appl. No.: 09/508,753

(22) PCT Filed: Sep. 17, 1998

(86) PCT No.: PCT/JP98/04167

§ 371 (c)(1),
(2), (4) Date: Jun. 16, 2000

(87) PCT Pub. No.: WO99/14364

PCT Pub. Date: Mar. 25, 1999

(30) Foreign Application Priority Data

Sep. 18, 1997 (JP) ................................. 9/270324

(51) Int. Cl.$^7$ ................................. C12Q 1/68

(52) U.S. Cl. .................... 435/6; 435/6; 435/91.1; 435/91.41; 435/91.5; 435/91.51; 435/91.52; 536/23.1; 536/24.33

(58) Field of Search ................. 435/6, 91.1, 91.41, 435/91.5, 91.51, 91.52; 536/23.1, 24.33

(56) References Cited

U.S. PATENT DOCUMENTS 5,597,713 A    1/1997 Kato et al.

FOREIGN PATENT DOCUMENTS

EP    625 572    11/1994

OTHER PUBLICATIONS

Hideaki Shinshi, Masanao Miwa, Kunio Kato, Masao Noguchi, Taijiro Matsushima and Takashi Sugimura, "A Novel Phosphodiesterase from Cultured Tobacco Cells", *Biochemistry*, vol. 15, No. 10 (1976), 2185–2190.

Suzuki, Y. et al., "Construction and Characterization of a full length–enriched cDNA library", *Gene* (1997, Nov.), vol. 200, No. 1/2, pp. 149–156.

Maruyama, K. et al., "Oligo–capping: a simple method to replace the cap structure of eukaryotic mRNAs with oligoribonucleotides", *Gene* (1994), vol. 138, No. 1/2, pp. 171–174.

Megumi Fujinaga, "PCR Method for Gene Amplification– Fundamentals and New Development", Dec. 10, 1990, Kyoritsu Shuppan K.K., p. 207–213. Including English language translation thereof.

Dudley et al., "Detection of Mouse Mammary Tumor Virus RNA in BALB/c Tumor Cell Line of Nonviral Etiologies", *J. Virol.* (1978), vol. 28, No. 3, pp. 743–752.

Shinshi, H. et al., "Enzyme Cleaving the 5'–Terminal Methylated Blocked Structure of Messenger RNA", *FEBS Letters* (1976), vol. 65, No. 2, pp. 254–257.

Genome Science: Special Edition of Dec. Issue of 'Protein, Nucleic Acid and Enzyme' (1997), Dec. 25, 1997, Kyoritsu Shuppan K.K., pp. 2836–2839. Including English language translation thereof.

Gubler et al., A Simple and Very Efficient Method for Generating cDNA libraries, *Gene*, (1983), vol. 25, pp. 263–269.

Okayama et al., "High–Efficiency Cloning for full–Length cDNA", *Molecular and Cellular Biology* (1982), vol. 2, pp. 161–170.

Frohman et al., "Rapid Production of Full–Length cDNAs from Rare Transcripts: Amplification Using a Single Gene–Specific Oligonucleotide Primer", *Proc. Natl. Acad. Sci., USA* (1998), vol. 85, pp. 8998–9002.

Furuichi et al., "A Blocked Structure at the 5'Terminus of mRNA from Cytoplasmic Polyhedrosis Virus", *Nature* (1975), vol. 253, pp. 374–375.

Tanpakughitsu·Kakusan·Kouso (Protein, Nucleic Acid and Enzyme), (1996) 41 (15), p. 2288.

Ohno, "Universal Rule for Coding Sequence Construction: TA/CG Deficiency–TG/CT Excess", *Proc. Natl. Acad. Sci. USA*, (1988), vol. 85, pp. 9630–9634.

Blumberg, D.D., "Creating a Ribonuclease–Free Environment", *Methods in Enzymology*, vol. 152, pp 20–24.

Higgins, S.J. and D.B. Hames, *RNA Processing a Practical Approach*, "Capping and Methylation of mRNA" by Furuichi et al., (1994), vol. II, pp. 35–67.

(List continued on next page.)

*Primary Examiner*—W. Gary Jones
*Assistant Examiner*—Janell E. Taylor
(74) *Attorney, Agent, or Firm*—Frishauf, Holtz, Goodman & Chick, P.C.

(57) ABSTRACT cDNA including the 5'-terminal sequence of full-length mRNA with a cap structure is synthesized from a mRNA sample containing the full-length mRNA with the cap structure and non-full-length mRNA without any cap structure in mixture. At the first step, the phosphate group at 5'-terminus of the non-full-length mRNA in the mRNA sample is removed. At the second step, the cap structure at the 5'-terminus of the full-length mRNA in the mRNA sample is removed. At the third step, an oligoribonucleotide is ligated to the phosphate group at 5'-terminus of mRNA generated through the first and second steps. At the fourth step, mRNA with the oligoribonucleotide ligated at the 5'-terminus thereof at the third step is subjected to a reverse transcriptase process using a short-chain oligonucleotide capable of being annealed to an intermediate sequence within the mRNA as primer, to synthesize a first-strand cDNA.

21 Claims, 6 Drawing Sheets

OTHER PUBLICATIONS

Wei et al., "Methylated Nucleotides Block 5'–Terminus of Vaccinia Virus Messenger RNA", *Proc. Natl. Sci. USA*, (1975), vol. 72, pp. 318–322.

Williams et al., "DNA Polymorphisms Amplified by Arbitrary Primers are Useful as Genetic Markers", *Nucleic Acids Research*, (1990), vol. 18, pp. 6531–6535.

Lipman et al., "Rapid and Sensitive Protein Similarity Searches", *Science*, (1985), vol. 227, pp. 1435–1441.

Riley et al., "A Novel, Rapid Mehod for the Isolation of Terminal Sequences from Yeast Artificial Chromosome (YAC) Clones", *Nucleic Acids Research*, (1990), vol. 18, pp. 2887–2890.

Chen et al., "The Human Growth Hormone Locus: Nucleotide Sequence, Biology, and Evolution", *Genomics*, vol. 4, pp. 479–497.

Tanaka et al., "cDNA Cloning of Human Chorionic Somatomammotropin–1 mRNA Whose Transcription was Initiated at the 5' Region of the TATA Box", *Biochemistry International*, (1988), vol. 16, pp. 287–292.

Valdes et al., "Island Rescue PCR: A Rapid and Efficient Method for Isolating Transcribed Sequences from Yeast Artificial Chromosomes and Cosmids", *Proc. Natl. Acad. Sci. USA*, (1994), vol. 91, pp. 5377–5381.

McClelland et al., "The Human Transferrin Receptor Gene: Genomic Organization, and the Complete Primary Structure of the Receptor Deduced from a cDNA Sequence", *Cell*, (1984), vol. 39, pp. 267–274.

Owen et al., "Noncoding 3' Sequences of the Transferrin Receptor Gene are Required for mRNA Regulation by Iron", *The EMBO Journal*, (1987), vol. 6, pp. 1287–1293.

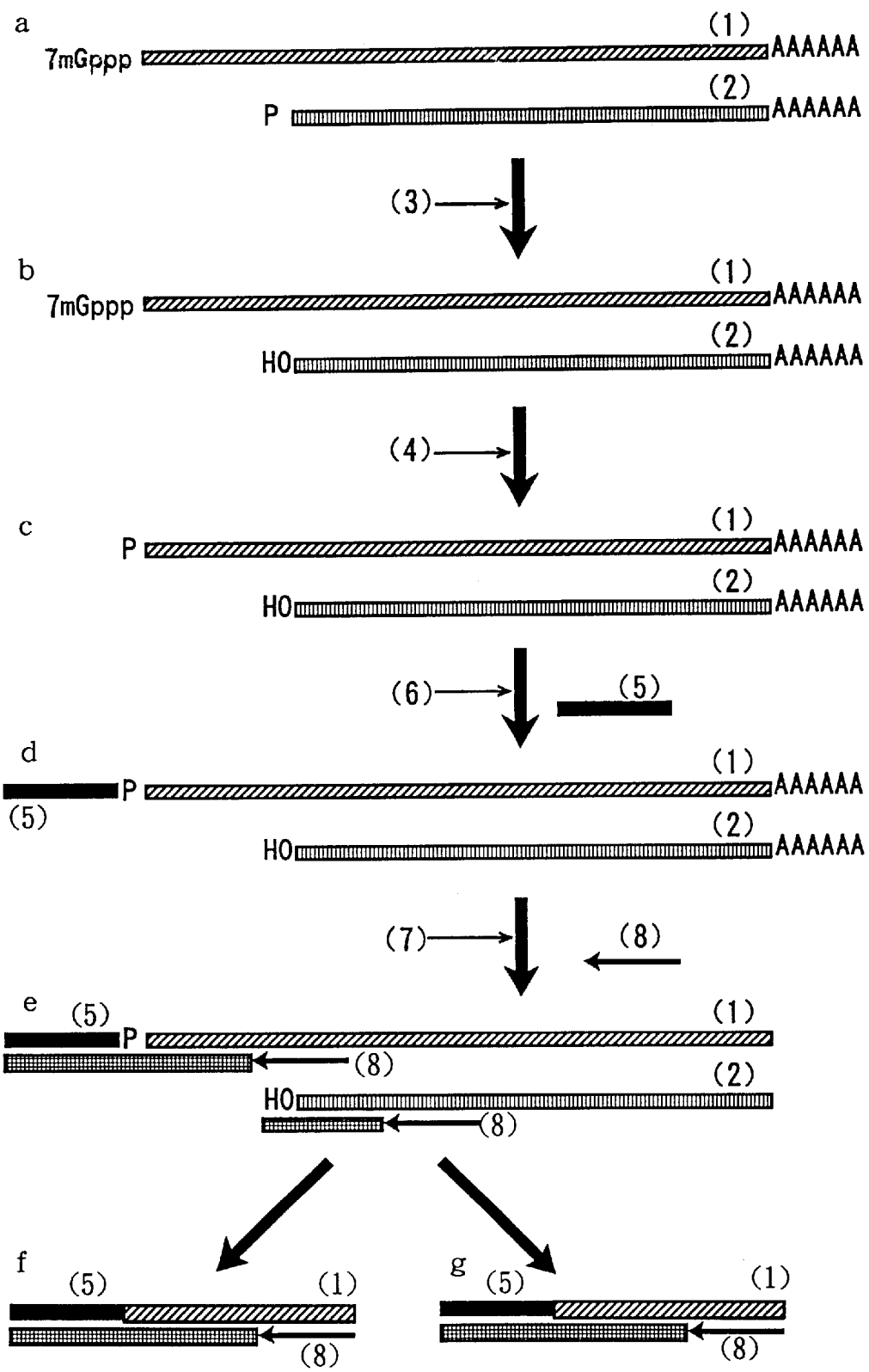
F i g. 1

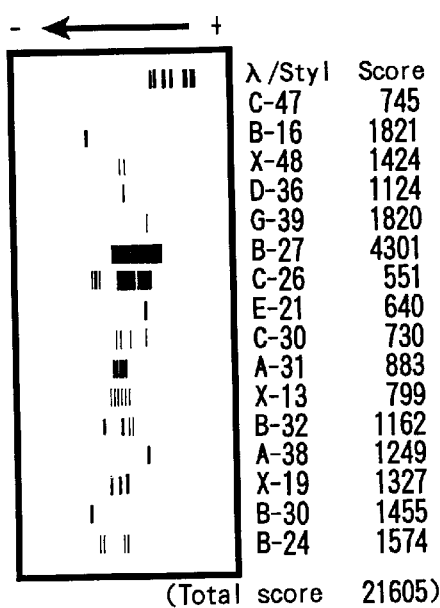

Fig. 5a

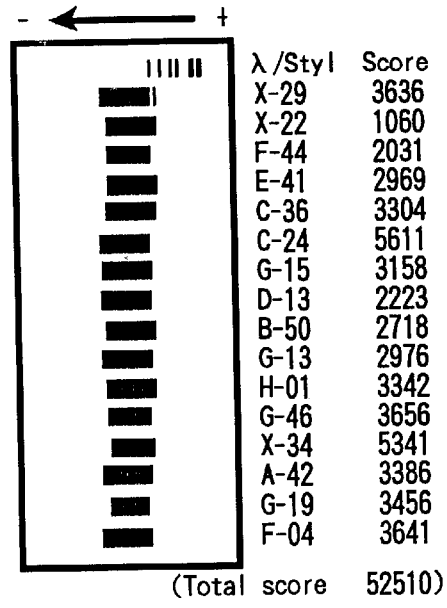

Fig. 5b

| 名称 | :配列（5'-3'） |
|---|---|
| GG | GUUGCGUUAC-ACAGCGUAUG-AUGCGUAAGG<br>(E-17)　　　(C-26)　　　(F-25) |
| AA | GUUGCGUUAC-ACAGCGUAUG-AUGCGUAA<br>(E-17)　　　(C-26)　　　(F-25) |
| GU | GUUGCGUUAC-ACAGCGUAUG-AUGCGU<br>(E-17)　　　(C-26)　　　(F-25) |
| RC+GU | AAGGUACGCC-GUUGCGUUAC-ACAGCGUAUG-AUGCGU<br>(O-35)　　　(E-17)　　　(C-26)　　　(F-25) |
| RC+AA | AAGGUACGCC-GUUGCGUUAC-ACAGCGUAUG-AUGCGUAA<br>(O-35)　　　(E-17)　　　(C-26)　　　(F-25) |
| RC2+GU | GUUGCGUUAC-AAGGUACGCC-ACAGCGUAUG-AUGCGU<br>(E-17)　　　(O-35)　　　(C-26)　　　(F-25) |
| RC2+AA | GUUGCGUUAC-AAGGUACGCC-ACAGCGUAUG-AUGCGUAA<br>(E-17)　　　(O-35)　　　(C-26)　　　(F-25) |
| vectorette | CGAAUCGUAA-CCGUUCGUAC-GAGAAUCGCU |

Fig. 6

M. φx174 DNA/HaeIII digest
1. Vectorette
2. RC2+AA
3. RC2+GU
4. RC+GU

MW maker: φx174DNA/HaeIII
lane 1-3: 1RC2&TRF3
lane 4-6: 1RC2&TRF4

SEQUENCE LISTING

```
<160> NUMBER OF SEQ ID NOS: 472

<210> SEQ ID NO 1
<211> LENGTH: 30
<212> TYPE: RNA
<213> ORGANISM: Artificial Sequence
<220> FEATURE:
```

```
<223> OTHER INFORMATION: Description of Artificial Sequence:
      Oligonucleotide

<400> SEQUENCE: 1
guugcguuac acagcguaug augcguaagg                                          30

<210> SEQ ID NO 2
<211> LENGTH: 28
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 2
guugcguuac acagcguaug augcguaa                                            28

<210> SEQ ID NO 3
<211> LENGTH: 26
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 3
guugcguuac acagcguaug augcgu                                              26

<210> SEQ ID NO 4
<211> LENGTH: 36
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 4
aagguacgcc guugcguuac acagcguaug augcgu                                   36

<210> SEQ ID NO 5
<211> LENGTH: 38
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 5
aagguacgcc guugcguuac acagcguaug augcguaa                                 38

<210> SEQ ID NO 6
<211> LENGTH: 36
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 6
guugcguuac aagguacgcc acagcguaug augcgu                                   36

<210> SEQ ID NO 7
<211> LENGTH: 38
<212> TYPE: RNA
<213> ORGANISM: Artificial Sequence
<220> FEATURE:
```

```
<223> OTHER INFORMATION: Description of Artificial Sequence:
      Oligonucleotide

<400> SEQUENCE: 7
guugcguuac aagguacgcc acagcguaug augcguaa                              38

<210> SEQ ID NO 8
<211> LENGTH: 30
<212> TYPE: RNA
<213> ORGANISM: Artificial Sequence
<220> FEATURE:
<223> OTHER INFORMATION: Description of Artificial Sequence: Vectorette
<300> PUBLICATION INFORMATION:
<301> AUTHORS: Valdas, JM., Tagle, DA. Colins, FS.
<302> TITLE: Island rescue PCR : a rapid and efficient method for
      isolating transcribed sequences from yeast artificial chromosomes
      and cosmid.
<303> JOURNAL: Proc. Natl. Acad. Sci. USA
<304> VOLUME: 91
<305> ISSUE: 12
<306> PAGES: 5377-5381
<307> DATE: 1994-06-07

<400> SEQUENCE: 8
cgaaucguaa ccguucguac gagaaucgcu                                       30

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer
<300> PUBLICATION INFORMATION:
<301> AUTHORS: Chen, E.Y., Liao, Y-C., Smith, D.H., Barrera-Saldana,
      H.A., Gelnas, R.E., Seeburg, P.H.
<302> TITLE: The human growth hormone locus : Nucleotide sequence,
      biology, and evolution
<303> JOURNAL: Genomics
<304> VOLUME: 4
<306> PAGES: 479-497
<307> DATE: 1989

<400> SEQUENCE: 9
gttggagggt gtcggaatag agtc                                             24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
gcgttacaca gcgtatgatg cgt                                              23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
gtacgccgtt gcgttacaca gc                                               22

<210> SEQ ID NO 12
<211> LENGTH: 24
<212> TYPE: DNA
<213> ORGANISM: Artificial Sequence
```

```
<220> FEATURE:
<223> OTHER INFORMATION: Description of Artificial Sequence: Primer

<400> SEQUENCE: 12
gcgttacaag gtacgccaca gcgt                                              24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
gtcctatgtg atgaccagtg atg                                               23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Primer
<300> PUBLICATION INFORMATION:
<301> AUTHORS: Valdas, J.M., Tagle, D.A., Colins, F.S.
<302> TITLE: Island rescue PCR : a rapid and efficient method for
      isolating transcribed sequences from yeast artificial chromosomes
      and cosmid.
<303> JOURNAL: Proc. Natl. Acad. Sci. USA
<304> VOLUME: 91
<305> ISSUE: 12
<306> PAGES: 5377-5381
<307> DATE: 1994-06-07

<400> SEQUENCE: 14
cgaatcgtaa ccgttcgtac gag                                               23

<210> SEQ ID NO 15
<211> LENGTH: 37
<212> TYPE: RNA
<213> ORGANISM: Artificial Sequence
<220> FEATURE:
<223> OTHER INFORMATION: Description of Artificial Sequence:
      Oligoribonucleotide

<400> SEQUENCE: 15
gaguccuaug cauaggacuc cugauacagc ugccagu                                37

<210> SEQ ID NO 16
<211> LENGTH: 37
<212> TYPE: RNA
<213> ORGANISM: Artificial Sequence
<220> FEATURE:
<223> OTHER INFORMATION: Description of Artificial Sequence:
      Oligoribonucleotide

<400> SEQUENCE: 16
gaguccuaug ugaugaccag ugaugaccag ugccagu                                37

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer
<300> PUBLICATION INFORMATION:
<301> AUTHORS: McClelland, A., Kuhn, L.C., Ruddle, F.H.
<302> TITLE: The human transferrin receptor gene : genomic organization,
      and the complete primary structure of the receptor deduced from a
      cDNA sequence.
```

```
<303> JOURNAL: Cell
<304> VOLUME: 39
<305> ISSUE: 2
<306> PAGES: 267-274
<307> DATE: 1984

<400> SEQUENCE: 17
gcttcacatt cttgctttct gagg                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer
<300> PUBLICATION INFORMATION:
<301> AUTHORS: McClelland, A., Kuhn, L.C., Ruddle, F.H.
<302> TITLE: The human transferrin receptor gene : genomic organization,
      and the complete primary structure of the receptor deduced from a
      cDNA sequence.
<303> JOURNAL: Cell
<304> VOLUME: 39
<305> ISSUE: 2
<306> PAGES: 267-274
<307> DATE: 1984

<400> SEQUENCE: 18
gcttgatggt gctggtgaag tctg                                              24

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 19
ctggagaaac                                                              10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 20
tctgaagagg                                                              10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 21
tttctcctgc                                                              10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 22
tgctggaaag                                                              10
```

-continued

```
<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 23
tgcgggaaac                                                           10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 24
agggaaaagg                                                           10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 25
actgctgaag                                                           10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 26
aacagaggag                                                           10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 27
atcctcttcc                                                           10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 28
acatcagcag                                                           10

<210> SEQ ID NO 29
<211> LENGTH: 10
<212> TYPE: DNA
<213> ORGANISM: Artificial Sequence
<220> FEATURE:
```

<223> OTHER INFORMATION: Description of Artificial Sequence: Primer

<400> SEQUENCE: 29
gagaagagtg                                                              10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 30
gagaaacagg                                                              10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 31
actgaggatg                                                              10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 32
acaaaggagg                                                              10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 33
aggaagacag                                                              10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 34
gacaaggatg                                                              10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 35
tgaggaaagc                                                              10

```
<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 36
ttctgcttcc                                                             10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 37
ggaaaagcag                                                             10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 38
ggacagaaag                                                             10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 39
agaccatctc                                                             10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 40
gtgacagaag                                                             10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 41
gtttctccag                                                             10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Primer
```

```
<400> SEQUENCE: 42
acaacaaggc                                                          10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 43
gtggtgaaag                                                          10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 44
ttcctttccc                                                          10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 45
tttcctcacc                                                          10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 46
accaccaaag                                                          10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 47
aatccagcag                                                          10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 48
gaaagagctg                                                          10

<210> SEQ ID NO 49
<211> LENGTH: 10
```

```
<212> TYPE: DNA
<213> ORGANISM: Artificial Sequence
<220> FEATURE:
<223> OTHER INFORMATION: Description of Artificial Sequence: Primer

<400> SEQUENCE: 49
ttctgtggac                                                          10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 50
aaaaggcagg                                                          10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 51
caccagaaac                                                          10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 52
tgaggtgaac                                                          10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 53
ctcctgaaac                                                          10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 54
ttctcaggag                                                          10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 55
```
cctgaaactg 10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 56
atctgggaac 10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 57
cagaaagacg 10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 58
actccttcag 10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 59
tgaaaccagc 10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 60
tgtctttgcc 10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 61
caatgctgag 10

<210> SEQ ID NO 62
<211> LENGTH: 10
<212> TYPE: DNA
<213> ORGANISM: Artificial Sequence

```
<220> FEATURE:
<223> OTHER INFORMATION: Description of Artificial Sequence: Primer

<400> SEQUENCE: 62
tgagagatgg                                                          10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 63
tggtgaagtc                                                          10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 64
cctgtttctc                                                          10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 65
tcagcaactg                                                          10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 66
ccgaaagaag                                                          10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 67
gaggtgaatg                                                          10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 68
gtcatcaagc                                                          10
```

```
<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 69
tgttttcccc                                                          10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 70
atttctgccc                                                          10

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 71
cagctctttc                                                          10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 72
aaaccacagc                                                          10

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 73
cactcttctc                                                          10

<210> SEQ ID NO 74
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 74
ctttctgtcc                                                          10

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Primer
```

```
<400> SEQUENCE: 75
cgaaaaccag                                                              10

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 76
ctgcttttcc                                                              10

<210> SEQ ID NO 77
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 77
gaatgaagcc                                                              10

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 78
ttgctgagtg                                                              10

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 79
gtttctggtg                                                              10

<210> SEQ ID NO 80
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 80
gaccaaagac                                                              10

<210> SEQ ID NO 81
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 81
attcctgtgg                                                              10

<210> SEQ ID NO 82
```

-continued

<210> SEQ ID NO 83
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 82
gagacacaac                                                              10

<210> SEQ ID NO 83
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 83
cccaaaacac                                                              10

<210> SEQ ID NO 84
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 84
gtgtttgtgc                                                              10

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 85
tttgctccag                                                              10

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 86
ctgatgacag                                                              10

<210> SEQ ID NO 87
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 87
ttcagaggtg                                                              10

<210> SEQ ID NO 88
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 88
aaaggtgagc                                                              10

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 89
atcacacacc                                                              10

<210> SEQ ID NO 90
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 90
gaatgccaac                                                              10

<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 91
cagtgatgac                                                              10

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 92
gtgacttctg                                                              10

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 93
tgctgaacag                                                              10

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 94
gtttcaggag                                                              10

<210> SEQ ID NO 95
<211> LENGTH: 10
<212> TYPE: DNA

<213> ORGANISM: Artificial Sequence
<220> FEATURE:
<223> OTHER INFORMATION: Description of Artificial Sequence: Primer

<400> SEQUENCE: 95
tgtcatcagc                                                          10

<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 96
acacaggaac                                                          10

<210> SEQ ID NO 97
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 97
tcatctgctc                                                          10

<210> SEQ ID NO 98
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 98
aaagcagacg                                                          10

<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 99
aagtcagagg                                                          10

<210> SEQ ID NO 100
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 100
caaatgccac                                                          10

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 101
tgagagtgag                                                          10

<210> SEQ ID NO 102
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 102
aatgccaacc                                                          10

<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 103
tgtggagttc                                                          10

<210> SEQ ID NO 104
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 104
cagaagtcac                                                          10

<210> SEQ ID NO 105
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 105
ttttctgccg                                                          10

<210> SEQ ID NO 106
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 106
aatctgctcc                                                          10

<210> SEQ ID NO 107
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 107
atccagttcc                                                          10

<210> SEQ ID NO 108
<211> LENGTH: 10
<212> TYPE: DNA
<213> ORGANISM: Artificial Sequence
<220> FEATURE:

```
<223> OTHER INFORMATION: Description of Artificial Sequence: Primer

<400> SEQUENCE: 108
gcacaaacac                                                              10

<210> SEQ ID NO 109
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 109
tcacaccaac                                                              10

<210> SEQ ID NO 110
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 110
cgtctttctg                                                              10

<210> SEQ ID NO 111
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 111
ctgtcatcag                                                              10

<210> SEQ ID NO 112
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 112
ctttcaccac                                                              10

<210> SEQ ID NO 113
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 113
tgatgaccag                                                              10

<210> SEQ ID NO 114
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 114
gcaaatggtg                                                              10
```

```
<210> SEQ ID NO 115
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 115
gtgttttggg                                                              10

<210> SEQ ID NO 116
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 116
cttctgtcac                                                              10

<210> SEQ ID NO 117
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 117
atggctgaac                                                              10

<210> SEQ ID NO 118
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 118
acaaggtcac                                                              10

<210> SEQ ID NO 119
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 119
gagcagattg                                                              10

<210> SEQ ID NO 120
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 120
gtcatcactg                                                              10

<210> SEQ ID NO 121
<211> LENGTH: 10
<212> TYPE: DNA
<213> ORGANISM: Artificial Sequence
<220> FEATURE:
<223> OTHER INFORMATION: Description of Artificial Sequence: Primer
```

```
<400> SEQUENCE: 121
gattcagagc                                                          10

<210> SEQ ID NO 122
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 122
tcagaccatc                                                          10

<210> SEQ ID NO 123
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 123
gattcagagg                                                          10

<210> SEQ ID NO 124
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 124
aatgccagag                                                          10

<210> SEQ ID NO 125
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 125
ggaactgaag                                                          10

<210> SEQ ID NO 126
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 126
gaaactgagc                                                          10

<210> SEQ ID NO 127
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 127
tctggttctc                                                          10

<210> SEQ ID NO 128
<211> LENGTH: 10
```

```
<212> TYPE: DNA
<213> ORGANISM: Artificial Sequence
<220> FEATURE:
<223> OTHER INFORMATION: Description of Artificial Sequence: Primer

<400> SEQUENCE: 128
aaaaaggggc                                                              10

<210> SEQ ID NO 129
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 129
accagtttcc                                                              10

<210> SEQ ID NO 130
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 130
catcaaccag                                                              10

<210> SEQ ID NO 131
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 131
gctcagtttc                                                              10

<210> SEQ ID NO 132
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 132
tggatgaacg                                                              10

<210> SEQ ID NO 133
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 133
tttctctcgg                                                              10

<210> SEQ ID NO 134
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 134
```

-continued gctctgaatc 10

<210> SEQ ID NO 135
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 135
actttctccg 10

<210> SEQ ID NO 136
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 136
ttcaccagtg 10

<210> SEQ ID NO 137
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 137
ctgctcaaac 10

<210> SEQ ID NO 138
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 138
attgctcagg 10

<210> SEQ ID NO 139
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 139
agttctgctc 10

<210> SEQ ID NO 140
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 140
cggaaaagtc 10

<210> SEQ ID NO 141
<211> LENGTH: 10
<212> TYPE: DNA
<213> ORGANISM: Artificial Sequence

```
<220> FEATURE:
<223> OTHER INFORMATION: Description of Artificial Sequence: Primer

<400> SEQUENCE: 141
ttttggctcc                                                              10

<210> SEQ ID NO 142
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 142
cagtttcagg                                                              10

<210> SEQ ID NO 143
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 143
gtctttggtc                                                              10

<210> SEQ ID NO 144
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 144
gaaagagtgg                                                              10

<210> SEQ ID NO 145
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 145
ggtgaacaac                                                              10

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 146
gatctcagac                                                              10

<210> SEQ ID NO 147
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 147
ctacaatgcc                                                              10
```

```
<210> SEQ ID NO 148
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 148
cgtgtttgag                                                          10

<210> SEQ ID NO 149
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 149
cctctgaatc                                                          10

<210> SEQ ID NO 150
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 150
caaactcacc                                                          10

<210> SEQ ID NO 151
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 151
tccctgtttg                                                          10

<210> SEQ ID NO 152
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 152
aacatctggc                                                          10

<210> SEQ ID NO 153
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 153
cttcagttcc                                                          10

<210> SEQ ID NO 154
<211> LENGTH: 10
<212> TYPE: DNA
<213> ORGANISM: Artificial Sequence
<220> FEATURE:
<223> OTHER INFORMATION: Description of Artificial Sequence: Primer
```

```
<400> SEQUENCE: 154
ggcttcattc                                                          10

<210> SEQ ID NO 155
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 155
tcaaacaggg                                                          10

<210> SEQ ID NO 156
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 156
aaacaccacg                                                          10

<210> SEQ ID NO 157
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 157
gttgtgtctc                                                          10

<210> SEQ ID NO 158
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 158
aatcagccac                                                          10

<210> SEQ ID NO 159
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 159
ctcagcattg                                                          10

<210> SEQ ID NO 160
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 160
actgaactcc                                                          10

<210> SEQ ID NO 161
```

```
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 161
actgagatcc                                                              10

<210> SEQ ID NO 162
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 162
tctttgctcg                                                              10

<210> SEQ ID NO 163
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 163
agggcaaaac                                                              10

<210> SEQ ID NO 164
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 164
tgaactggtc                                                              10

<210> SEQ ID NO 165
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 165
ctttctaccc                                                              10

<210> SEQ ID NO 166
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 166
taagccatcc                                                              10

<210> SEQ ID NO 167
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 167
```
ctggttttcg                                                              10

<210> SEQ ID NO 168
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 168
ttgccacttc                                                              10

<210> SEQ ID NO 169
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 169
ttgttcccag                                                              10

<210> SEQ ID NO 170
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 170
gtgaatggtg                                                              10

<210> SEQ ID NO 171
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 171
tggattggtc                                                              10

<210> SEQ ID NO 172
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 172
acagaggttc                                                              10

<210> SEQ ID NO 173
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 173
ccacaaatcc                                                              10

<210> SEQ ID NO 174
<211> LENGTH: 10
<212> TYPE: DNA

```
<213> ORGANISM: Artificial Sequence
<220> FEATURE:
<223> OTHER INFORMATION: Description of Artificial Sequence: Primer

<400> SEQUENCE: 174
agtcctgaac                                                          10

<210> SEQ ID NO 175
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 175
ggtgagtttg                                                          10

<210> SEQ ID NO 176
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 176
actgacacag                                                          10

<210> SEQ ID NO 177
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 177
gtgagttcac                                                          10

<210> SEQ ID NO 178
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 178
tctggtttcg                                                          10

<210> SEQ ID NO 179
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 179
tttgtgccac                                                          10

<210> SEQ ID NO 180
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 180
gtgaactcac                                                          10
```

<210> SEQ ID NO 181
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 181
aacacatccg                                                          10

<210> SEQ ID NO 182
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 182
gtacaagtcc                                                          10

<210> SEQ ID NO 183
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 183
aggtggtttc                                                          10

<210> SEQ ID NO 184
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 184
agccattctg                                                          10

<210> SEQ ID NO 185
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 185
ggatttgtgg                                                          10

<210> SEQ ID NO 186
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 186
tgaacacacc                                                          10

<210> SEQ ID NO 187
<211> LENGTH: 10
<212> TYPE: DNA
<213> ORGANISM: Artificial Sequence
<220> FEATURE:

<223> OTHER INFORMATION: Description of Artificial Sequence: Primer

<400> SEQUENCE: 187
aagagtggtg                                                              10

<210> SEQ ID NO 188
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 188
cattcacctc                                                              10

<210> SEQ ID NO 189
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 189
tggctgattg                                                              10

<210> SEQ ID NO 190
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 190
ccactctttc                                                              10

<210> SEQ ID NO 191
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 191
tgaactgtgc                                                              10

<210> SEQ ID NO 192
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 192
gcttgatgac                                                              10

<210> SEQ ID NO 193
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 193
gtggcatttg                                                              10

<210> SEQ ID NO 194
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 194
tgctcagttg                                                              10

<210> SEQ ID NO 195
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 195
ggattcactg                                                              10

<210> SEQ ID NO 196
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 196
tgaaatgccc                                                              10

<210> SEQ ID NO 197
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 197
aaacaggtgc                                                              10

<210> SEQ ID NO 198
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 198
cgctgaaatc                                                              10

<210> SEQ ID NO 199
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 199
ctgattcagg                                                              10

<210> SEQ ID NO 200
<211> LENGTH: 10
<212> TYPE: DNA
<213> ORGANISM: Artificial Sequence
<220> FEATURE:
<223> OTHER INFORMATION: Description of Artificial Sequence: Primer

```
<400> SEQUENCE: 200
tggttttgcg                                                              10

<210> SEQ ID NO 201
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 201
gtttgagcag                                                              10

<210> SEQ ID NO 202
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 202
aaagtgccac                                                              10

<210> SEQ ID NO 203
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 203
acattggcag                                                              10

<210> SEQ ID NO 204
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 204
cttctttcgg                                                              10

<210> SEQ ID NO 205
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 205
caccatttgc                                                              10

<210> SEQ ID NO 206
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 206
gatcatggtc                                                              10

<210> SEQ ID NO 207
<211> LENGTH: 10
```

```
<212> TYPE: DNA
<213> ORGANISM: Artificial Sequence
<220> FEATURE:
<223> OTHER INFORMATION: Description of Artificial Sequence: Primer

<400> SEQUENCE: 207
cacctgatac                                                              10

<210> SEQ ID NO 208
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 208
cacttttccg                                                              10

<210> SEQ ID NO 209
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 209
catccttgtc                                                              10

<210> SEQ ID NO 210
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 210
caccattcac                                                              10

<210> SEQ ID NO 211
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 211
gtaatggtgg                                                              10

<210> SEQ ID NO 212
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 212
agccagtttc                                                              10

<210> SEQ ID NO 213
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 213
```
acagtgctac 10

<210> SEQ ID NO 214
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 214
caatctgctc 10

<210> SEQ ID NO 215
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 215
aatgacagcg 10

<210> SEQ ID NO 216
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 216
tactgttgcc 10

<210> SEQ ID NO 217
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 217
ggaactacag 10

<210> SEQ ID NO 218
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 218
tgaacaggtg 10

<210> SEQ ID NO 219
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 219
acttttggcg 10

<210> SEQ ID NO 220
<211> LENGTH: 10
<212> TYPE: DNA
<213> ORGANISM: Artificial Sequence

```
<220> FEATURE:
<223> OTHER INFORMATION: Description of Artificial Sequence: Primer

<400> SEQUENCE: 220
atttctgcgg                                                              10

<210> SEQ ID NO 221
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 221
tcaacatcgc                                                              10

<210> SEQ ID NO 222
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 222
agcacaatgg                                                              10

<210> SEQ ID NO 223
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 223
ggaaccaatc                                                              10

<210> SEQ ID NO 224
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 224
tgcctcattg                                                              10

<210> SEQ ID NO 225
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 225
tcttgagcag                                                              10

<210> SEQ ID NO 226
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 226
aaaggcatcg                                                              10
```

```
<210> SEQ ID NO 227
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 227
aggcaaactg                                                            10

<210> SEQ ID NO 228
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 228
ctcaaacacg                                                            10

<210> SEQ ID NO 229
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 229
acctttcacc                                                            10

<210> SEQ ID NO 230
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 230
gaaactcacg                                                            10

<210> SEQ ID NO 231
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 231
gatttcagcg                                                            10

<210> SEQ ID NO 232
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 232
gttggcattc                                                            10

<210> SEQ ID NO 233
<211> LENGTH: 10
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 233
ttttctgcgg                                                                10

<210> SEQ ID NO 234
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 234
catctgactg                                                                10

<210> SEQ ID NO 235
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 235
ttggctgtac                                                                10

<210> SEQ ID NO 236
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 236
ccgtgaaaag                                                                10

<210> SEQ ID NO 237
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 237
gcagattgtc                                                                10

<210> SEQ ID NO 238
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 238
ttgcaggttg                                                                10

<210> SEQ ID NO 239
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 239
ccagattgtc                                                                10

<210> SEQ ID NO 240
```

```
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 240
ctggttgatg                                                              10

<210> SEQ ID NO 241
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 241
ccaccattac                                                              10

<210> SEQ ID NO 242
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 242
agtgacatcg                                                              10

<210> SEQ ID NO 243
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 243
aatctcaccc                                                              10

<210> SEQ ID NO 244
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 244
atttcagccg                                                              10

<210> SEQ ID NO 245
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 245
ctatccagtc                                                              10

<210> SEQ ID NO 246
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 246
```

```
tgaggtttgc                                                              10

<210> SEQ ID NO 247
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 247
gatgagttcg                                                              10

<210> SEQ ID NO 248
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 248
cttacctgac                                                              10

<210> SEQ ID NO 249
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 249
gttgttcacc                                                              10

<210> SEQ ID NO 250
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 250
atacacccac                                                              10

<210> SEQ ID NO 251
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 251
gtatcaggag                                                              10

<210> SEQ ID NO 252
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 252
cagtggtatg                                                              10

<210> SEQ ID NO 253
<211> LENGTH: 10
<212> TYPE: DNA
```

```
<213> ORGANISM: Artificial Sequence
<220> FEATURE:
<223> OTHER INFORMATION: Description of Artificial Sequence: Primer

<400> SEQUENCE: 253
cctgaatcag                                                          10

<210> SEQ ID NO 254
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 254
tgacagtcac                                                          10

<210> SEQ ID NO 255
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 255
gactggatag                                                          10

<210> SEQ ID NO 256
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 256
tttgtcaccg                                                          10

<210> SEQ ID NO 257
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 257
aatggtctgc                                                          10

<210> SEQ ID NO 258
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 258
aaaagacccg                                                          10

<210> SEQ ID NO 259
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 259
tggtaaaggg                                                          10
```

<210> SEQ ID NO 260
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 260
cattaccagc                                                                10

<210> SEQ ID NO 261
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 261
gatctgacac                                                                10

<210> SEQ ID NO 262
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 262
ttcattcccg                                                                10

<210> SEQ ID NO 263
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 263
cattactgcg                                                                10

<210> SEQ ID NO 264
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 264
ctacaagtcc                                                                10

<210> SEQ ID NO 265
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 265
cataccactg                                                                10

<210> SEQ ID NO 266
<211> LENGTH: 10
<212> TYPE: DNA
<213> ORGANISM: Artificial Sequence
<220> FEATURE:

<223> OTHER INFORMATION: Description of Artificial Sequence: Primer

<400> SEQUENCE: 266
tcaccctttg                                                          10

<210> SEQ ID NO 267
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 267
tttgagcacg                                                          10

<210> SEQ ID NO 268
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 268
aaacctgtcg                                                          10

<210> SEQ ID NO 269
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 269
gtaccagtac                                                          10

<210> SEQ ID NO 270
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 270
gacaatctgg                                                          10

<210> SEQ ID NO 271
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 271
gctgtatcag                                                          10

<210> SEQ ID NO 272
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 272
cgtgagtttc                                                          10

```
<210> SEQ ID NO 273
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 273
tgccagtatg                                                              10

<210> SEQ ID NO 274
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 274
ggcattgtag                                                              10

<210> SEQ ID NO 275
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 275
gtcaggtaag                                                              10

<210> SEQ ID NO 276
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 276
gcaagtgtag                                                              10

<210> SEQ ID NO 277
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 277
gtcctgatac                                                              10

<210> SEQ ID NO 278
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 278
cataccagac                                                              10

<210> SEQ ID NO 279
<211> LENGTH: 10
<212> TYPE: DNA
<213> ORGANISM: Artificial Sequence
<220> FEATURE:
<223> OTHER INFORMATION: Description of Artificial Sequence: Primer
```

<400> SEQUENCE: 279
tttcacaccg                                                        10

<210> SEQ ID NO 280
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 280
ctgcttgatg                                                        10

<210> SEQ ID NO 281
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 281
gacaatctgc                                                        10

<210> SEQ ID NO 282
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 282
cgaactcatc                                                        10

<210> SEQ ID NO 283
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 283
tacaacgagg                                                        10

<210> SEQ ID NO 284
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 284
gtatcaggac                                                        10

<210> SEQ ID NO 285
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 285
gcgtttgatg                                                        10

<210> SEQ ID NO 286
<211> LENGTH: 10

```
<212> TYPE: DNA
<213> ORGANISM: Artificial Sequence
<220> FEATURE:
<223> OTHER INFORMATION: Description of Artificial Sequence: Primer

<400> SEQUENCE: 286
gctggtaatg                                                           10

<210> SEQ ID NO 287
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 287
cagtatcagc                                                           10

<210> SEQ ID NO 288
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 288
gaaaatccgc                                                           10

<210> SEQ ID NO 289
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 289
cagtgaatcc                                                           10

<210> SEQ ID NO 290
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 290
tgaaagtccg                                                           10

<210> SEQ ID NO 291
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 291
aaatggacgc                                                           10

<210> SEQ ID NO 292
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 292
```
agcagatacg 10

<210> SEQ ID NO 293
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 293
ttatccctg 10

<210> SEQ ID NO 294
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 294
cagtatggtg 10

<210> SEQ ID NO 295
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 295
tcagattgcg 10

<210> SEQ ID NO 296
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 296
gcttacttcc 10

<210> SEQ ID NO 297
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 297
cactaaaggg 10

<210> SEQ ID NO 298
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 298
gctcagtatc 10

<210> SEQ ID NO 299
<211> LENGTH: 10
<212> TYPE: DNA
<213> ORGANISM: Artificial Sequence

```
<220> FEATURE:
<223> OTHER INFORMATION: Description of Artificial Sequence: Primer

<400> SEQUENCE: 299
tatgtgagcg                                                              10

<210> SEQ ID NO 300
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 300
tcgcatcaac                                                              10

<210> SEQ ID NO 301
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 301
gatactgagc                                                              10

<210> SEQ ID NO 302
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 302
ctacacttgc                                                              10

<210> SEQ ID NO 303
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 303
gtctggtatg                                                              10

<210> SEQ ID NO 304
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 304
gcggattttc                                                              10

<210> SEQ ID NO 305
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 305
gtttacctcc                                                              10
```

<210> SEQ ID NO 306
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 306
agggaatac                                                                10

<210> SEQ ID NO 307
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 307
ctgatacagc                                                                10

<210> SEQ ID NO 308
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 308
catcaaacgc                                                                10

<210> SEQ ID NO 309
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 309
attcgtggag                                                                10

<210> SEQ ID NO 310
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 310
cttttcacgg                                                                10

<210> SEQ ID NO 311
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 311
cgtaaagcac                                                                10

<210> SEQ ID NO 312
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 312
ggaggtaaac                                                                 10

<210> SEQ ID NO 313
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 313
cggagtttac                                                                 10

<210> SEQ ID NO 314
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 314
acttgtcacg                                                                 10

<210> SEQ ID NO 315
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 315
aacgagagag                                                                 10

<210> SEQ ID NO 316
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 316
tgactgttcg                                                                 10

<210> SEQ ID NO 317
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 317
cccctatttg                                                                 10

<210> SEQ ID NO 318
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 318
atgactaccg                                                                 10

<210> SEQ ID NO 319

```
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 319
actgtttcgg                                                              10

<210> SEQ ID NO 320
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 320
tgacggcaac                                                              10

<210> SEQ ID NO 321
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 321
aggtaaagcg                                                              10

<210> SEQ ID NO 322
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 322
ggctattctc                                                              10

<210> SEQ ID NO 323
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 323
gaaaacgtgg                                                              10

<210> SEQ ID NO 324
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 324
tttatggggc                                                              10

<210> SEQ ID NO 325
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 325
```
tagttgcctg                                                                         10

<210> SEQ ID NO 326
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 326
tcggatttgc                                                                         10

<210> SEQ ID NO 327
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 327
agtgggttac                                                                         10

<210> SEQ ID NO 328
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 328
gctgatactg                                                                         10

<210> SEQ ID NO 329
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 329
tttcaccgtg                                                                         10

<210> SEQ ID NO 330
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 330
ggacttgtag                                                                         10

<210> SEQ ID NO 331
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 331
tctgacgatg                                                                         10

<210> SEQ ID NO 332
<211> LENGTH: 10
<212> TYPE: DNA

```
<213> ORGANISM: Artificial Sequence
<220> FEATURE:
<223> OTHER INFORMATION: Description of Artificial Sequence: Primer

<400> SEQUENCE: 332
caaaaacggg                                                              10

<210> SEQ ID NO 333
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 333
agtgtaaggg                                                              10

<210> SEQ ID NO 334
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 334
gtaaactccg                                                              10

<210> SEQ ID NO 335
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 335
gtgccttatc                                                              10

<210> SEQ ID NO 336
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 336
accctatctc                                                              10

<210> SEQ ID NO 337
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 337
tgtaatccgc                                                              10

<210> SEQ ID NO 338
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 338
cactaacacc                                                              10
```

<210> SEQ ID NO 339
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 339
ccactatctg                                                          10

<210> SEQ ID NO 340
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 340
ggagtttacg                                                          10

<210> SEQ ID NO 341
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 341
gtgctttacg                                                          10

<210> SEQ ID NO 342
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 342
caccatactg                                                          10

<210> SEQ ID NO 343
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 343
gaaacgatgg                                                          10

<210> SEQ ID NO 344
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 344
atttggtcgg                                                          10

<210> SEQ ID NO 345
<211> LENGTH: 10
<212> TYPE: DNA
<213> ORGANISM: Artificial Sequence
<220> FEATURE:

-continued

<223> OTHER INFORMATION: Description of Artificial Sequence: Primer

<400> SEQUENCE: 345
cagatagtgg                                                                10

<210> SEQ ID NO 346
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 346
agtgcttacc                                                                10

<210> SEQ ID NO 347
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 347
cacggaaatg                                                                10

<210> SEQ ID NO 348
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 348
ttcggtgatg                                                                10

<210> SEQ ID NO 349
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 349
gataaggcac                                                                10

<210> SEQ ID NO 350
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 350
ctgtagttcc                                                                10

<210> SEQ ID NO 351
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 351
ccacgttttc                                                                10

```
<210> SEQ ID NO 352
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 352
tgattggtcg                                                          10

<210> SEQ ID NO 353
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 353
ggtgttagtg                                                          10

<210> SEQ ID NO 354
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 354
catcgtgttg                                                          10

<210> SEQ ID NO 355
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 355
cgtaaactcc                                                          10

<210> SEQ ID NO 356
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 356
ccctttagtg                                                          10

<210> SEQ ID NO 357
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 357
cgcagtaatg                                                          10

<210> SEQ ID NO 358
<211> LENGTH: 10
<212> TYPE: DNA
<213> ORGANISM: Artificial Sequence
<220> FEATURE:
<223> OTHER INFORMATION: Description of Artificial Sequence: Primer
```

<400> SEQUENCE: 358
gcagattacg                                                              10

<210> SEQ ID NO 359
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 359
cccgttttg                                                               10

<210> SEQ ID NO 360
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 360
caaaacgctg                                                              10

<210> SEQ ID NO 361
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 361
gctcaatacg                                                              10

<210> SEQ ID NO 362
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 362
ttcgctgatg                                                              10

<210> SEQ ID NO 363
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 363
ttagcatccg                                                              10

<210> SEQ ID NO 364
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 364
tatcgctgtc                                                              10

<210> SEQ ID NO 365
<211> LENGTH: 10

```
<212> TYPE: DNA
<213> ORGANISM: Artificial Sequence
<220> FEATURE:
<223> OTHER INFORMATION: Description of Artificial Sequence: Primer

<400> SEQUENCE: 365
acgggtaaag                                                         10

<210> SEQ ID NO 366
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 366
tacaccgaac                                                         10

<210> SEQ ID NO 367
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 367
gagaatagcc                                                         10

<210> SEQ ID NO 368
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 368
actaatgggc                                                         10

<210> SEQ ID NO 369
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 369
aatagcctcc                                                         10

<210> SEQ ID NO 370
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 370
cctaatcagc                                                         10

<210> SEQ ID NO 371
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 371
```
gtgataaccg 10

<210> SEQ ID NO 372
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 372
gatctaaggc 10

<210> SEQ ID NO 373
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 373
gagtcctatg 10

<210> SEQ ID NO 374
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 374
aaactccgtc 10

<210> SEQ ID NO 375
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 375
cgtattgagc 10

<210> SEQ ID NO 376
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 376
agtcaacgtc 10

<210> SEQ ID NO 377
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 377
gctgattagg 10

<210> SEQ ID NO 378
<211> LENGTH: 10
<212> TYPE: DNA
<213> ORGANISM: Artificial Sequence

```
<220> FEATURE:
<223> OTHER INFORMATION: Description of Artificial Sequence: Primer

<400> SEQUENCE: 378
caaatagggg                                                              10

<210> SEQ ID NO 379
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 379
agccgaaatg                                                              10

<210> SEQ ID NO 380
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 380
cgttatgagc                                                              10

<210> SEQ ID NO 381
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 381
gatcatagcc                                                              10

<210> SEQ ID NO 382
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 382
tttttccgcc                                                              10

<210> SEQ ID NO 383
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 383
cgtaatctgc                                                              10

<210> SEQ ID NO 384
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 384
actgataccg                                                              10
```

<210> SEQ ID NO 385
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 385
tttctgcgtc                                                                 10

<210> SEQ ID NO 386
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 386
catttccgtg                                                                 10

<210> SEQ ID NO 387
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 387
cagcgatttc                                                                 10

<210> SEQ ID NO 388
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 388
cggttatcac                                                                 10

<210> SEQ ID NO 389
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 389
gaaatcgctg                                                                 10

<210> SEQ ID NO 390
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 390
tattgagcgg                                                                 10

<210> SEQ ID NO 391
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 391
atgaacggtg                                                              10

<210> SEQ ID NO 392
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 392
atgaagcgac                                                              10

<210> SEQ ID NO 393
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 393
ggtactaagg                                                              10

<210> SEQ ID NO 394
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 394
agtgcgaaag                                                              10

<210> SEQ ID NO 395
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 395
cataggactc                                                              10

<210> SEQ ID NO 396
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 396
gtatgacgac                                                              10

<210> SEQ ID NO 397
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 397
cagcgttttg                                                              10

<210> SEQ ID NO 398

```
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 398
tcgatacagg                                                            10

<210> SEQ ID NO 399
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 399
gatttaccgc                                                            10

<210> SEQ ID NO 400
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 400
ggaagtaagc                                                            10

<210> SEQ ID NO 401
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 401
ttcgttctgc                                                            10

<210> SEQ ID NO 402
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 402
caacacgatg                                                            10

<210> SEQ ID NO 403
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 403
caaacggatg                                                            10

<210> SEQ ID NO 404
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 404
```
ttacgctgtg                                                                10

<210> SEQ ID NO 405
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 405
tgctcatacg                                                                10

<210> SEQ ID NO 406
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 406
gcgtatgttg                                                                10

<210> SEQ ID NO 407
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 407
gatcaatcgc                                                                10

<210> SEQ ID NO 408
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 408
acgggtaatg                                                                10

<210> SEQ ID NO 409
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 409
aaagtccgtg                                                                10

<210> SEQ ID NO 410
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 410
tgttatgccg                                                                10

<210> SEQ ID NO 411
<211> LENGTH: 10
<212> TYPE: DNA

```
<213> ORGANISM: Artificial Sequence
<220> FEATURE:
<223> OTHER INFORMATION: Description of Artificial Sequence: Primer

<400> SEQUENCE: 411
acggatgtag                                                              10

<210> SEQ ID NO 412
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 412
aaacgctctg                                                              10

<210> SEQ ID NO 413
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 413
ccatcgtttc                                                              10

<210> SEQ ID NO 414
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 414
aaatgacgcc                                                              10

<210> SEQ ID NO 415
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 415
atcgccatac                                                              10

<210> SEQ ID NO 416
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 416
taaaacgccc                                                              10

<210> SEQ ID NO 417
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 417
gacattcgtg                                                              10
```

```
<210> SEQ ID NO 418
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 418
gctcataacg                                                          10

<210> SEQ ID NO 419
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 419
caacatacgc                                                          10

<210> SEQ ID NO 420
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 420
gatcatagcg                                                          10

<210> SEQ ID NO 421
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 421
gatcgcattg                                                          10

<210> SEQ ID NO 422
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 422
accaaacgac                                                          10

<210> SEQ ID NO 423
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 423
tacctaagcg                                                          10

<210> SEQ ID NO 424
<211> LENGTH: 10
<212> TYPE: DNA
<213> ORGANISM: Artificial Sequence
<220> FEATURE:
```

```
<223> OTHER INFORMATION: Description of Artificial Sequence: Primer

<400> SEQUENCE: 424
tgttatcccg                                                              10

<210> SEQ ID NO 425
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 425
gttttcgcag                                                              10

<210> SEQ ID NO 426
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 426
attcgcagtg                                                              10

<210> SEQ ID NO 427
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 427
gaacggatac                                                              10

<210> SEQ ID NO 428
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 428
accgtgattc                                                              10

<210> SEQ ID NO 429
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 429
gcggtaaatc                                                              10

<210> SEQ ID NO 430
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 430
ctgtcgtttc                                                              10
```

```
<210> SEQ ID NO 431
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 431
ccgactattc                                                             10

<210> SEQ ID NO 432
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 432
gatctaaccg                                                             10

<210> SEQ ID NO 433
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 433
aatacacggg                                                             10

<210> SEQ ID NO 434
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 434
catccgtttg                                                             10

<210> SEQ ID NO 435
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 435
cacgaatgtc                                                             10

<210> SEQ ID NO 436
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 436
accgttgttc                                                             10

<210> SEQ ID NO 437
<211> LENGTH: 10
<212> TYPE: DNA
<213> ORGANISM: Artificial Sequence
<220> FEATURE:
<223> OTHER INFORMATION: Description of Artificial Sequence: Primer
```

<400> SEQUENCE: 437
tgcgacaatc                                                              10

<210> SEQ ID NO 438
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 438
tcggtcatag                                                              10

<210> SEQ ID NO 439
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 439
agcgttcatc                                                              10

<210> SEQ ID NO 440
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 440
agagcgatac                                                              10

<210> SEQ ID NO 441
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 441
gtaacgcaac                                                              10

<210> SEQ ID NO 442
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 442
ataaccgcac                                                              10

<210> SEQ ID NO 443
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 443
acccgtttac                                                              10

<210> SEQ ID NO 444
<211> LENGTH: 10

```
<212> TYPE: DNA
<213> ORGANISM: Artificial Sequence
<220> FEATURE:
<223> OTHER INFORMATION: Description of Artificial Sequence: Primer

<400> SEQUENCE: 444
gatcacgtac                                                          10

<210> SEQ ID NO 445
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 445
acggtcatac                                                          10

<210> SEQ ID NO 446
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 446
tattgacgcc                                                          10

<210> SEQ ID NO 447
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 447
gtcgtcatac                                                          10

<210> SEQ ID NO 448
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 448
caatagcgac                                                          10

<210> SEQ ID NO 449
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 449
aatacgccac                                                          10

<210> SEQ ID NO 450
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 450
```
gtttacggtg                                                                     10

<210> SEQ ID NO 451
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 451
tctactcgtg                                                                     10

<210> SEQ ID NO 452
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 452
tgaccgtaac                                                                     10

<210> SEQ ID NO 453
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 453
gatttacgcg                                                                     10

<210> SEQ ID NO 454
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 454
gtatccgttc                                                                     10

<210> SEQ ID NO 455
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 455
acatacgagc                                                                     10

<210> SEQ ID NO 456
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 456
caccgtaaac                                                                     10

<210> SEQ ID NO 457
<211> LENGTH: 10
<212> TYPE: DNA
<213> ORGANISM: Artificial Sequence

```
<220> FEATURE:
<223> OTHER INFORMATION: Description of Artificial Sequence: Primer

<400> SEQUENCE: 457
gttcgtaagc                                                              10

<210> SEQ ID NO 458
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 458
tccgtatgtc                                                              10

<210> SEQ ID NO 459
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 459
tgcgacatac                                                              10

<210> SEQ ID NO 460
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 460
cccgtaaatc                                                              10

<210> SEQ ID NO 461
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 461
gtcgctattg                                                              10

<210> SEQ ID NO 462
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 462
tgattagcgg                                                              10

<210> SEQ ID NO 463
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 463
tgacgatagc                                                              10
```

```
<210> SEQ ID NO 464
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 464
gcttacgaac                                                              10

<210> SEQ ID NO 465
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 465
gaatagtcgg                                                              10

<210> SEQ ID NO 466
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 466
gttgcgttac                                                              10

<210> SEQ ID NO 467
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 467
acagcgtatg                                                              10

<210> SEQ ID NO 468
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 468
atgcgtaagg                                                              10

<210> SEQ ID NO 469
<211> LENGTH: 50
<212> TYPE: DNA
<213> ORGANISM: Homo sapiens

<400> SEQUENCE: 469
tataaaaagg gcccacaaga gaccggctct aggatcccaa ggcccaactc                   50

<210> SEQ ID NO 470
<211> LENGTH: 20
<212> TYPE: DNA
<213> ORGANISM: Homo sapiens

<400> SEQUENCE: 470
aggatcccaa ggcccaactc                                                   20
```

-continued

```
<210> SEQ ID NO 471
<211> LENGTH: 19
<212> TYPE: DNA
<213> ORGANISM: Homo sapiens

<400> SEQUENCE: 471
ggatcccaag gcccaactc                                              19

<210> SEQ ID NO 472
<211> LENGTH: 12
<212> TYPE: DNA
<213> ORGANISM: Homo sapiens

<400> SEQUENCE: 472
aaggcccaac tc                                                     12
```

METHOD FOR SYNTHESIZING CDNA FROM MRNA SAMPLE

BACKGROUND OF THE INVENTION

1. Field of the Invention

The present invention relates to a method for synthesizing cDNA from a mRNA sample and to tobacco acid pyrophosphatase for use in the method; more specifically, the invention relates to a rapid synthesis method of cDNA including the 5'-terminal region of mRNA in a sample for the analysis of a nucleotide sequence derived from the 5'-terminus of the mRNA.

2. Background of the Invention

Numerous types of proteins composing cell are present, such as proteins involved in cell morphology, proteins involved in development or proteins involved in metabolism. The patterns of the presence undoubtedly determine the properties of cell. Essential information relating to the mode of these presence and functions is imprinted in the gene in cell and is realized by mRNA as a copy of the gene. mRNA functions as template for protein translation and also as a carrier of the information flow from DNA to protein. Ultimately, mRNA reflects the "phenotypes" in all biological organisms. These proteins are industrially valuable and possibly applicable as pharmaceutical drugs, diagnostic agents, bio-sensors and bio-reactors, provided that these proteins are biologically active substances. Hence, it is very important to recover full-length mRNA and procure gene information from the mRNA. Recent progress in the gene recombinant technology and more recent promotion in the genome analysis project are now permitting cDNA cloning and analysis technology readily usable.

Although rapid analysis of complete 5"-terminal sequence of mRNA has increasingly been demanded in recent years, no technology has been established yet to enable such rapid analysis in a simple and rapid fashion. Because the 5'-terminal sequence of full-length mRNA contains a transcription start for gene expression analysis on genome, rapid analysis of the 5'-terminal sequence as well as enormous quantities of sequenced genome open up a way for transcription gene mapping. Furthermore, accurate information of the 5'-terminal sequence of mRNA can identify the sequences of gene expression regulatory promoters present upstream. These promoters are cis-factors regulating when, where and how much a gene should be expressed. The detection of the 5'-terminal sequence of mRNA verifies that an upstream promoter sequence is functional, which suggests a new possibility for the etiological analysis or diagnosis or therapeutic treatment of diseases.

Practically, the information as to when, where and how much a gene is expressed is very valuable information for the etiological analysis or diagnosis or therapeutic treatment of diseases. The Human Genome Project currently promoted internationally mentions as one of the goals to collect such information. The ultimate purpose of the Project lies in the nucleotide sequencing of biological genome. The nucleotide sequences of several bacterial genome species and the nucleotide sequences in the whole genome of budding yeast have already been sequenced and reported. Most of many genes identified on the isolated genome species are functionally not yet identified, which is a big issue in future. In that sense, the significance of the analysis of cDNA reflecting the gene expression dynamics in cell is increasingly drawing attention.

Herein, by the term cDNA referred to as complementary DNA is meant DNA synthetically prepared by reverse transcriptase using mRNA as template. In other words, the information of mRNA encoding the information of the amino acid sequence of protein is synthetically constructed as cDNA. The analysis of the cDNA can readily determine the primary structure of the protein and can readily promote the development of a large-scale expression system. Thus, such cDNA preparation is now very important, industrially.

Ideally, the ultimate goal of the cDNA cloning technology lies in the replacement of all expressed mRNAs with complete cDNAs. Thus, the information is greatly valuable. In other words, the information recovered from such full-length cDNA serves as a starting point for the analysis of the information on genome, because the information includes the information of transcription start and the entire information of expressed protein. The primary protein sequence recovered from a complete coding sequence distinctively shortens the time required for the functional analysis.

However, the technology for the recovery of cDNA including full-length mRNA has been a not-yet matured technology "still under way of development" among the DNA technologies in rapid progress. For example, the Gubler-Hoffman method (Gene, Vol. 25, pp. 236–269, 1983) is known as one of synthesis method of cDNAs commonly applied conventionally. Nevertheless, many of cDNAs synthesized by the method are incomplete with terminal deficiency. Alternatively, the Okayama-Berg method (Mol. Cell. Biol., Vol. 2, pp. 161–170, 1982) is a synthesis method characteristic in that full-length cDNA is readily prepared. Even by the method, however, reverse transcription sometimes stops in the course of cDNA synthesis, so no guarantee is given to the resulting cDNA that it is of full length.

The RACE method (Rapid amplification of cDNA ends: Proc. Natl. Aca. Sci. USA, Vol. 85, pp. 8998–9002, 1988) has been suggested as a method to supplement a portion lacking in cDNA, based on the partial cDNA sequences recovered by the existing methods, so as to acquire the complete information of mRNA. The method comprises reverse transcription based on a target cDNA sequence to add a homopolymer to both the ends of cDNA by terminal transferase or to ligate an adapter comprising a synthesized DNA to both the ends of cDNA by T4 DNA ligase, and polymerase chain reaction (PCR) based on these added sequences and a primer specific to the target cDNA, thereby analyzing only the terminal regions of mRNA sequence.

The analysis of the target 5'-terminus of mRNA in particular by the method (referred to as 5'-RACE) can be done in a very simple fashion, because PCR is utilized by the method. Accordingly, the method is frequently used. Principally, however, the method apparently cannot analyze the 5'-terminal sequence of mRNA used for the preparation of the cDNA, although the method can analyze the 5'-terminus of cDNA. Hence, the recovery of complete 5'-terminus of mRNA is very difficult, compared with the recovery of complete 3'-terminus by 3'-RACE, in which poly-A sequence is responsible for the protection role against terminal deficiency. As described above, even currently, the method is acclaimed as a "not-yet established technology".

It is known that the 5'-terminus of complete mRNA has a characteristic structure called cap structure (Nature, Vol. 253, pp. 374–375, 1975). An attempt has been suggested to analyze cDNA, targeting the vicinity of the cap structure (Japanese Patent Laid-open No. 6-153953 (1994); Gene, Vol. 138, pp. 171–174, 1994).

According to these methods, tobacco acid pyrophosphatase (referred to as "TAP" hereinafter) specifically cleaving the cap structure is used. These methods comprise treating mRNA with alkali phosphatase to remove the phosphate group from the 5'-terminus of mRNA without any cap, subsequently treating the resulting mRNA with TAP to cleave the cap, adding an oligoribonucleotide and continuously effecting reverse transcription, to synthesize cDNA. Although these methods are complicated because enzymatic reactions continue over plural steps, these methods are a few effective methods principally capable of specifically analyzing full-length mRNA. Nevertheless, these methods include problems to be improved in the steps. Currently, therefore, these methods are not commonly widespread, although these methods are greatly needed due to the significance of the 5'-terminal sequencing as described above.

SUMMARY OF THE INVENTION

It is an object of the present invention to provide a synthesis method of cDNA from mRNA, so as to recover the complete 5'-terminal sequence of cDNA at a large-scale in a rapid manner by selectively synthesizing cDNA including the 5'-terminal sequence of full-length mRNA with the cap structure. It is another object of the present invention to provide tobacco acid pyrophosphatase preferable for use in the synthesis method.

The present invention proposes to attain the above-mentioned objective by suggesting a DNA synthesis method for synthesizing cDNA including the 5'-terminal sequence of full-length mRNA with a cap structure from a mRNA sample containing the full-length mRNA with the cap structure and non-full-length mRNA without any cap structure in mixture, said method comprising:

a first step of removing the phosphate group at the 5'-terminus of the non-full-length mRNA in the mRNA sample;

a second step of removing the cap structure at the 5'-terminus of the full-length mRNA in the mRNA sample;

a third step of ligating an oligonucleotide of a predetermined sequence to the phosphate group at the 5'-terminus of the mRNA generated through the first and second steps in the sample; and a fourth step of subjecting the mRNA ligated with the oligonucleotide at the phosphate group at the 5'-terminus to a reverse transcriptase process using as primer a short-chain oligonucleotide capable of being annealed to an intermediate sequence within the mRNA, to synthesize a first-strand cDNA;

characterized in that said oligoribonucleotide for use at the third step has a sequence recovered by preparing a number of oligoribonucleotide sequences including various combinations of bases in a predetermined number, carrying out a homology search with a predetermined nucleotide sequence data base to determine the occurrence number of a sequence completely matching or differing by one base, and preparing a combination of plural sequences in a low-frequency occurrence group including a sequence at the lowest occurrence number.

According to a preferred embodiment of the present invention, the third step comprises ligating an oligoribonucleotide of a predetermined sequence to the phosphate group.

According to another embodiment of the present invention, the third step comprises ligating an oligoribonucleotide composed of a sequence never contained in the sequence of the mRNA in the mRNA sample to the phosphate group.

Specifically, as the oligonucleotide, use is made of an oligoribonucleotide comprising a 10-base or longer sequence never contained in the sequence of the mRNA. More specifically, a great number of oligonucleotide sequences are prepared, the oligonucleotide sequences comprising various combinations of oligonucleotides of bases in a predetermined number; a homology search of each of the oligonucleotide sequences with a predetermined nucleotide sequence data base is then carried out; the occurrence number of a sequence completely matching or differing by one base is determined; by using combinations of plural sequences in the low occurrence frequency group including a sequence of the lowest occurrence frequency, a sequence is determined and an oligoribonucleotide of this sequence is used. In one embodiment of the invention, any one of the following oligoribonucleotides is used as such oligoribonucleotide.

5'-GUUGCGUUAC-ACAGCGUAUG-AUGCGUA AGG-3'
5'-GUUGCGUUAC-ACAGCGUAUG-AUGCGUAA-3'
5'-GUUGCGUUAC-ACAGCGUAUG-AUGCGU-3'
5'-AAGGUACGCC-GUUGCGUUAC-ACAGCGUA UG-AUGCGU-3'
5'-AAGGUACGCC-GUUGCGUUAC-ACAGCGUA UG-AUGCGUAA-3'
5'-GUUGCGUUAC-AAGGUACGCC-ACAGCGUA UG-AUGCGU-3'
5'-GUUGCGUUAC-AAGGUACGCC-ACAGCGUA UG-AUGCGUAA-3'

According to still another embodiment of the present invention, the primer to be used at the fourth step is a short-chain oligonucleotide of a length of 6 bases or longer.

According to still another embodiment of the present invention, the cap structure at the 5-terminus of the full-length mRNA in the mRNA sample is removed by using tobacco acid pyrophosphatase purified to a high purity with no contamination of trace amounts of nuclease cleaving the phosphodiester bond comprising RNA and a phosphatase removing 5-phosphate group freshly generated after cap cleavage.

The present invention also proposes a method for synthesizing cDNA including the 5'-terminal sequence of full-length mRNA with a cap structure from a mRNA sample containing the full-length mRNA with the cap structure and non-full-length mRNA without any cap structure in mixture, the method comprising:

a first step of removing the phosphate group at the 5'-terminus of the non-full-length mRNA in the mRNA sample;

a second step of removing the cap structure at the 5'-terminus of the full-length mRNA in the mRNA sample by using tobacco acid pyrophosphatase highly purified by using alkali phosphatase;

a third step of ligating an oligoribonucleotide of a predetermined sequence to the phosphate group at the 5'-terminus of mRNA generated through the first and second steps in the sample, said oligoribonucleotide comprising a sequence never contained in the sequence of mRNA in the mRNA sample;

a fourth step of subjecting the mRNA ligated with the oligoribonucleotide at the phosphate group at the 5'-terminus to a reverse transcriptase process using as primer a short-chain oligonucleotide of 6 bases or more in length and with an ability being annealed to an intermediate sequence within the mRNA, to synthesize a first-strand cDNA; and a fifth step of synthesizing a second-strand cDNA based on the resulting first-strand cDNA.

As the tobacco acid pyrophosphatase for use in the cDNA synthesis method of the present invention, it is preferable to use the tobacco acid pyrophosphatase which can remove the cap structure at the 5'-terminus and has already been purified at an extent such that the tobacco acid pyrophosphatase substantially never contains other enzymes cleaving the remaining sites within mRNA.

In accordance with the method of the present invention, only cDNA containing the 5'-terminal sequence of full-length mRNA with the cap structure is synthesized from a mRNA sample containing the full-length mRNA and non-full-length mRNA without the cap structure in mixture. Accordingly, it is preferable to preliminarily remove the phosphate group at the 5'-terminus of the non-full-length mRNA in the sample, thereby avoiding the occurrence of the additional reaction of oligonucleotide (preferably oligoribonucleotide) at the third step.

As to the full-length mRNA in the sample, it is preferable to remove the cap structure at the 5'-terminus of the full-length mRNA in the mRNA sample at the second step and then, in the third step, an oligonucleotide is ligated to the phosphate group thus generated at the fresh 5'-terminus of the mRNA. Prior to this reaction, the phosphate group at the 5'-terminus of the non-full-length mRNA is already removed. Thus, the additional reaction never progresses in the non-full-length mRNA.

As the oligonucleotide, use is preferably made of oligoribonucleotide, because the reaction efficiency of an enzyme T4 RNA ligase when used differs in the order of two digits between substrates RNA and DNA.

At the fourth step, subsequently, mRNA with the oligonucleotide ligated at the phosphate group at the 5'-terminus thereof is subjected to a reverse transcriptase process using as primer a short-chain oligonucleotide to be annealed to an intermediate sequence within the mRNA. Thus, a complementary first-strand cDNA is synthesized. In such manner, cDNA can be synthesized readily, starting from the 5'-terminus of mRNA.

Preferably, the fifth step is satisfactrrily added to synthesize a double-stranded cDNA from a single-stranded cDNA. The fifth step comprises additionally synthesizing a second-strand cDNA from the resulting first-strand cDNA.

One characteristic aspect of the present invention lies in the use as primer of a short-chain oligonudeotide ("random hexamer" of 6 bases, in particular, in accordance with the present invention) capable of being annealed to an intermediate sequence within mRNA, preferably a sequence in the vicinity of the 5'-terminus.

For more detailed description of the characteristic aspect, the present invention relates to a method for converting the information of mRNA to cDNA. General methods comprise synthesizing a complementary DNA using reverse transcriptase and RNA as template. Then, primer is needed for the initiation of the reaction with the reverse transcriptase. The term primer means DNA chain or RNA chain supplying nucleotide 3'-OH required by a template-dependent DNA polymerase for the synthesis of a new chain. Current progress of DNA synthesis technology enables ready synthesis of short-chain oligonucleotides of 15 to 40 bases in length and with a primer function.

For the purpose of cDNA synthesis, generally, use is made of oligo $dT_{12-18}$ primer complementary to a sequence of a series of plural adenines, as called poly-A chain, present on the 3'-terminus of mRNA. Although the synthesis efficiently starts in case that the primer is used, the synthesis rarely progresses up to the 5'-terminus of mRNA with the cap structure because of the instability and long chain of RNA and the secondary structure thereof, as described above. It is readily deduced that the tendency is likely more prominent in case that mRNA is longer. More additionally, the aforementioned grounds work to make full-length cDNA synthesis difficult. It cannot be said that any of the existing technologies attempting full-length cDNA synthesis can overcome the problem.

On the contrary, in accordance with the present invention, the 5'-terminal sequence of mRNA, in particular, can absolutely be analyzed rapidly, which has been considered difficult. One of the characteristic features of the present invention lies in the use as primer of a short-chain oligonucleotide capable of being annealed to an intermediate sequence within mRNA, preferably a sequence in the vicinity of the 5'-terminus. Particularly preferably, a short-chain oligonucleotide comprising a random sequence of 6 bases or more.

Theoretically, herein, the base length of the short-chain oligonucleotide used as the primer is an appropriate length shorter than the sequence of mRNA, in which reverse transcription can start from various sites of mRNA. It is currently reported that the shortest length required for sequence-specific primer activity is a length of 6 bases. Thus, the single-stranded oligonucleotide is of a length of 6 bases or longer in accordance with the invention.

In case that the shortest random hexamer comprising 6 bases is used as primer, principally, single-stranded oligonucleotides of 4096 ($=4^6$) nucleotide sequences are nominated as candidates. Among such numerous sequences, accordingly, a single-stranded oligonucleotide of a nucleotide sequence capable of initiating reverse transcription in a desired site of mRNA is satisfactorily selected. When such random hexamer is selected, the possibility of the synthesis of cDNA including the 5'-terminus of mRNA can be raised.

A reverse transcription method using a short-chain oligonucleotide of such appropriate nucleotide sequence is frequently utilized as the search method of clones along 5'-direction, for the cloning of cDNA derived from large mRNA. The method is described in for example J. Virol., Vil. 28, p. 743 (1978).

However, the procedure described in the method in J. Viol. and the procedure of the method according to the present invention are identical in terms of reverse transcription by means of short-chain oligonucleotide but are totally different in that only 5' cDNA is selectively amplified by the procedure according to the present invention. Because the method described in J. Virol. comprises reverse transcription, and subsequent synthesis of a second strand and integration thereof in a vector, clones where reverse transcription has never progressed up to 5'-terminus are generated; and furthermore, generally, a linker DNA is attached for the insertion into a vector. During the course of the attachment of the linker DNA, the linker DNA is linked to the termini of a double-stranded cDNA. Therefore, the termini are blunt ended by using T4 DNA polymerase. In that course, 10 to 50 nucleotides are removed, so that full-length cDNA cannot be generated, consequently. In other words, no 5'-terminal sequence is recovered. Alternatively, the method according to the present invention is specific in that an oligoribonucleotide is specifically ligated only to full-length mRNA and that immediately after reverse transcription, PCR is carried out using a primer specific to the sequence of the oligoribonucleotide, to thereby selectively amplify only cDNA comprising complete 5'-terminal sequence.

An additional aspect of the present invention relates to the sequence of an oligoribonucleotide to be replaced for the 5'-terminal cap structure removed with TAP process. The oligoribonucleotide is ligated to the 5'-terminus of mRNA and is then synthesized in the form of cDNA through reverse transcription. The oligoribonucleotide works as a attachment site of a primer specific to the oligoribonucleotide, when used. Thus, the sequence serves as a very important marker for the analysis of the complete 5'-terminus. Reverse transcription using the random hexamer, in particular, enables the collection of plural cDNA fragments derived from mRNA; hence, the sequence specificity of the oligonucleotide replaced for the cap in these fragments determines whether or not only the sequence derived from the 5'-terminus of the mRNA can specifically be analyzed. In accordance with the present invention, therefore, the designing of the oligoribonucleotide and the sequencing thereof are very significant.

For more detailed description, it is said that the nucleotide sequence on the genome of humans or mouse comprises about $3\times10^9$ base pairs (bp). Gene-encoding regions, gene expression regulatory regions, reiterative sequences, introns and the like are arranged on the genome and these structures function under the control of extremely sophisticated programs in the course of development. It is also considered that the sequences are never random.

For example, a structure designated "CpG island" is listed. The structure is known to be present in the 5'-region, promoter region and first exon of gene (Tanpakushitsu.Kakusan.Kouso (Protein, Nucleic acid and Enzyme), 41 (15), p. 2288, (1996)). It is known that promoters involved in gene expression or regions involved in transcription termination are enriched with AT. The following reason is very readily understandable but is just deduced; the CpG island serves as a landmark for protein as a trans-factor controlling gene expression to speedily discriminate AT rich region thermodynamically unstable from GC rich region thermodynamically stable, when the protein is going to find its attachment site from the sequences on genome.

Furthermore, it is known based on the analyses so far that the occurrence frequency of dinucleotides is biased in all living organisms. Particularly, a rule of excess CT and TG and deficiency of CG and TA is also known (Proc. Natl. Acad. Sci., Vol. 85, pp. 9630–9634 (1988)). It is thus considered that the genome sequences are never random in living organisms but include information evolved under a certain rule.

Regarding to the oligoribonucleotide for use in accordance with the present invention, therefore, the application of a sequence introduced under consideration of the bias in the sequences on genome to the analysis of the 5'-terminal sequence of mRNA can elevate the precision of the analysis of the 5'-terminus of a specific gene among an assembly of very complicated 5'-cDNA sequences.

In association with the present invention, additionally, it has been deduced that TAP quality is a very significant element. More specifically, it has been known that the cap structure can be cleaved by using TAP (FEBS Lett., Vol. 65, pp. 254–257 (1976)). The method is only one known method capable of principally verifying the cap. The TAP action absolutely certifies that RNA has the cap structure (7 mGppp) at the 5'-terminus of mRNA, namely RNA with intact 5'-terminus.

Meanwhile, it is known that RNA is handled with much difficulty, because RNase as one nuclease species consistently exposes RNA to a degradation risk. Thus, RNA experiments essentially demand the handling of RNA under suppression of the activity at the lowest limit as required. A reference (Blumberg, D. D. Method in Enz., 152: pp. 20–24 (1987), Academic Press.) for example describes in detail experimental precautions relating to the handling. Even under such precautions, it is difficult to thoroughly suppress RNA degradation. Additionally, mRNA differs from genome DNA in that mRNA is not double-stranded but single-stranded. Accordingly, RNA extracted should be handled in aqueous solvents. However, the most thermodynamically stable stem structure is formed as the RNA secondary structure in various regions within the molecule. The stem structure is a serious cause for the inhibition of reverse transcriptase reaction. The aforementioned two points serve as serious causes for incomplete conversion of mRNA sequence to cDNA.

In an additional characteristic aspect of the present invention, tobacco acid pyrophosphatase is used so as to remove the phosphate group from the cap structure at the 5'-terminus of non-full-length mRNA in the mRNA sample at the second step; the tobacco acid pyrophosphatase in particular can remove the cap structure at the 5'-terminus and is already purified at an extent with no contamination of other enzymes cleaving the remaining sites of mRNA.

Specifically, it is confirmed that TAP currently commercially available is not appropriately used for efficient sequencing of the 5'-terminus of mRNA. Because the TAP contains trace amounts of enzymes such as nuclease cleaving phosphodiester bonds composing RNA and phosphatase removing 5'-phosphate group freshly generated after cap cleavage, such TAP can never be used for selective cleavage of the cap structure in mRNA and thereby efficient sequencing of the 5'-terminus of mRNA. In accordance with the present invention, therefore, use is made of TAP being capable of removing the cap structure at the 5'-terminus and purified at an extent with no contamination of other enzymes cleaving the remaining sites of mRNA.

As has been described above in accordance with the present invention, advantageously, a rapid synthesis method of cDNA starting from the 5'-terminus of mRNA can be provided for the purpose of the analysis of the full-length 5'-terminal sequences of numerous cDNA species in a rapid manner by selectively synthesizing cDNA including the 5'-terminal sequence of full-length mRNA with the cap structure. Additionally, tobacco acid pyrophosphatase preferable for use in the synthesis method can be provided.

BRIEF DESCRIPTION OF THE DRAWINGS

FIG. 1 shows an explanatory diagram schematically depicting the schemes of the individual steps in the cDNA synthesis method according to one embodiment of the present inventiion;

FIG. 5 shows an explanatory diagram depicting the RAPD analysis results of selected primers of 10-mer sequence using human genome DNA as template vs. the homolog scores thereof; FIG. 5a expresses group 1; and FIG. 5b expresses group 2;

FIG. 6 depicts the sequences of 9 oligoribonucleotides functioning as primers;

FIG. 9 shows an explanatory diagram of the PCR amplification results of the transferrin receptor 5' cDNA derived from the human placenta oligo capping cDNA.

BEST MODE FOR CARRYING OUT THE INVENTION

EXAMPLE 1

Scheme of cDNA Synthesis Method

Figure 2:
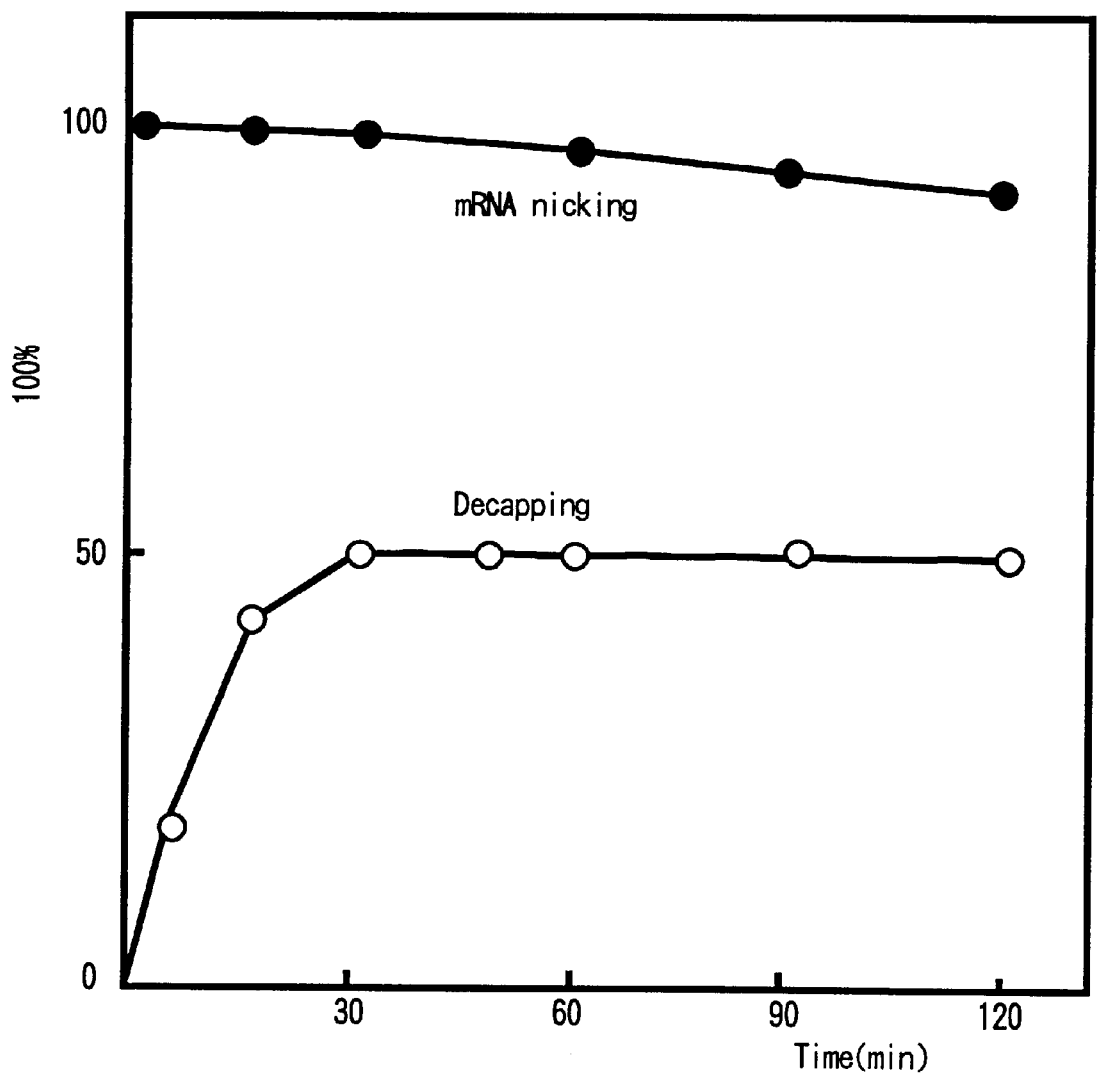
FIG. 2 shows graphs depicting the results of the removal of the cap structure with highly purified TAP without any damage of the RNA chain.

FIG. 1 shows an explanatory diagram depicting the scheme of each step of the cDNA synthesis method according to one embodiment of the present invention. The process of the cDNA synthesis method according to the present embodiment comprises:

a first step of adding alkali phosphatase 3 to a mRNA sample containing full-length mRNA 1 with the cap structure (7 mGppp) and non-full-length mRNA 2 without any cap structure in mixture as shown in the starting step a, to remove the 5'-terminal phosphate group P of the non-full-length mRNA 2 with the alkali phosphatase, as shown in step b, a second step of adding tobacco acid pyrophosphatase 4 to the mRNA sample to remove the 5'-terminal cap structure (7 mGppp) of the full-length mRNA in the mRNA sample by using the tobacco acid pyrophosphatase, as shown in the step c, a third step of ligating oligoribonucleotide 5 to the 5'-terminal phosphate group of the resulting mRNA with T4 RNA ligase 6 as shown in the step d, and a fourth step of adding to the mRNA sample, reverse transcriptase 7 and random hexamer 8 capable of being annealed to an intermediate sequence within the mRNA, to synthesize a first-strand cDNA complementary by subjecting the mRNA ligated with the oligoribonucleotide at the 5'-terminal phosphate group to a process with the reverse transcriptase using the random hexamer as primer, as shown in the step e.

More preferably, the process further conprises an additional fifth step of synthesizing a second-strand cDNA from the first-strand cDNA as shown in the step f and optionally amplifying the resulting second-strand cDNA by PCR as shown in the step g.

For example, DNA carrying the 5'-terminal sequence of the mRNA can be prepared on the basis of the cDNA thus prepared. The thus prepared DNA can ultimately attain the purpose of the present invention, when the DNA is cloned in an appropriate vector and is then sequenced. Based on the sequence of the oligoribonucleotide, furthermore, the first-strand cDNA synthesized by the reverse transcriptase reaction can be converted to a double-stranded cDNA. 5'-cDNA library can be prepared by cloning the double-stranded cDNA in for example plasmid vector or phage vector.

As has been described above, in accordance with the present invention, the 5'-terminus of mRNA can be sequenced completely for subjects of plural genes.

EXAMPLE 2

Purification and Examination of Tobacco Acid Pyrophosphatase (TAP)

In the method of the present invention, it has been revealed that the purification degree of TAP as an enzyme recognizing and cleaving the cap structure is very important for the complete sequencing of the 5'-terminus of mRNA. More specifically, TAP can be commercially available in many countries. However, the present inventor's attempts have demonstrated that the TAP commercially available can never be used for efficient determination of the 5'-terminal sequence of mRNA. The reason is as follows. So as to selectively cleave the cap structure of mRNA, it is never permitted that TAP is contaminated with even trace amounts of nuclease cleaving the phosphodiester bond composing RNA and phosphatase removing the 5'-phosphate group freshly generated after the cleavage of the cap. Such TAP commercially available is contaminated with nuclease and phosphatase, although the TAP is at some degree of purity. Thus, the TAP can never be used for efficient determination of the 5'-terminal sequence of mRNA.

In other words, these commercially available TAP products cleave RNA during the course of the cleavage of the cap structure due to the contamination of nuclease, so it has been found for the first time by a highly sensitive assay method developed by the present inventors, that these TAP products absolutely cannot be used therefor. Only the highly sensitive assay method can determine whether or not a TAP enzyme sample is contaminated with nuclease. General nuclease assay methods can never determine whether the purity of TAP is high enough for use for the determination of the nucleotide sequence of the 5'-terminus of mRNA in the vicinity of the cap. In other words, one of the essential aspects of the present invention includes high purification of TAP to remove nuclease and phosphatase from the TAP.

Alternatively, the highly sensitive assay method for purity evaluation serves as a measure to enable the high purification of TAP and determines whether or not the purified TAP can be used in the method of the present invention. The highly sensitive assay method will be described below. According to the method, TAP can be purified to prepare the high-purity TAP enzyme required for the process of the present invention.

TAP purification is already described in a reference (Biochemistry, Vol.15 (10), pp. 2185–2190 (1976)). However, present inventors removed the contaminated nuclease and the like by various combinations of column chromatographic means or by repeating a single type of chromatography, as long as the results of the activity assay by the highly sensitive assaying were not satisfactory. It should be noted that the enzyme is extremely labile and the recovery of an enzyme sample with a high specific activity is very significant for the following experiments. But the enzyme is not limited to the example herein described. More detailed explanations are as follows.

Tobacco cell BY2 was kindly supplied by Dr. Hideaki Sinshi of the Life Engineering and Industrial Technology Research Institute, the Agency of Industrial Science and Technology of Japan. The cell was cultured according to the reference described above. More specifically, as the culture medium, use was made of the Murashige-Scoog culture medium; the cell was cultured under shaking under a dark condition for 7 days; and the cell was harvested by centrifugation. In one typical example, the cell of 180 g was recovered from a 1.5-liter culture broth.

The cell was suspended in 300 mL of 200 mM NaCl, 10 m β-mercaptoethanol (β-ME), 1 mM ethylenediaminetetraacetate disodium (EDTA), and 100 mM sodium acetate, pH 5.0, and was then disrupted with Sonifier-450 (Trademark; manufactured by Bronson, Co.) while care was taken not to raise the temperature. By centrifugation, the cell debris was discarded from the disrupted cell; and the resulting supernatant was thoroughly dialyzed against 10 mM β-ME, 20% glycerin, 0.01% Triton X-100, and 10 mM Tris-HCl, pH 6.9 (25° C.).

The dialysate was subjected to chromatography on DE52 column (™; manufactured by Wattman, Co.); and the pass-through fraction was adsorbed on S-Sepharose (™; manufactured by Pharmacia, Co.). The column was sufficiently washed until no ultraviolet-absorbing materials were eluted; and the absorbed substance was eluted on a linear gradient of 0–0.5 M NaCl concentrations. As a TAP fraction, the eluted fraction was added to 1 mM EDTA containing 5 mM nitrophenyl-pT (manufactured by Sigma, Co.), 0.1% β-ME, 0.01% Triton X-100, and 50 mM sodium acetate, pH 6.0. The resulting mixture was kept at 37° C. for 10 minutes. Then, the absorbance at O.D. 400 nm was measured for the assay. Active fractions were combined together; after desalting, the resulting mixture was subjected to gel-filtration chromatography on a column of Sephacryl S-200 (™; manufactured by Pharmacia, Co.), to assay the TAP activity in the same manner as described above.

The active fractions were combined together; after desalting, the resulting mixture was subjected to gel-filtration chromatography on a column High-trap Blue (™; manufactured by Pharmacia, Co.), to elute the absorbed substance on a linear gradient of 0–0.5M concentrations. The active fractions were assayed and sufficiently dialyzed against a stock buffer (50% glycerin, 100 mM NaCl, 0.1 mM EDTA, 1 mM dithiothreitol (DTT), 0.1 mM benzamidine, 0.01% Triton X-100, 10 mM Tris-HCl, pH 6.9); and the resulting dialysate was stored at −20° C. until use. In one typical example, a TAP sample of 0.05 U/μL or mL can be recovered by the aforementioned procedures. In case that the contamination of a trace amount of nuclease was observed by the ultra-super sensitive purity assay method, the aforementioned procedures were repeated; and additionally, desalting and gel-filtration column chromatography on Sephacryl S-200 (™; manufactured by Pharmacia, Co.) were repeated.

The activity then was defined as follows; 1 U of the enzyme can release 1 μ mole p-nitrophenol during the reaction at 37° C. for one minute under the assay conditions of the activity. In the case of a commercially available TAP product (manufactured by Wako Pure Chemicals, Co. Ltd.), it is defined that 1 U of the enzyme can release 1 nmol inorganic phosphoric acid from a substrate ATP during the reaction under conditions in the presence of 50 mM sodium acetate, pH 5.5, 1 mM EDTA, and 10 mM β-ME at 37° C. for 30 minutes. As to the relative activity of the TAP sample of the present example to the commercially available product, 1U of the TAP sample of the present example for p-nitrophenol corresponds to the 367,000 U activity of the commercially available product for ATP as substrate. Thus, 0.5 U of the TAP sample recovered in the previous purification example is converted to 185,500 U. Hereinafter, the activity of TAP is expressed on conversion to the latter definition of the activity.

At that state, the level of contaminating nuclease was assayed, using as substrate 8 μg of rRNA (16S and 23S) of *Escherichia coli*. More specifically, the TAP corresponding to 500 U was added to and reacted with rRNA of *Escherichia coli* in a buffer of 1 mM EDTA, 0.1% β-ME, 0.01% Triton X-100, 5 mM sodium acetate, pH 6.0, for reaction at 37° C. for 2 hours. The RNA was electrophoresed on 0.1% agarose under a modification condition of formamide presence; the electrophoresis was terminated when a concurrently added dye xylene cyanol reached about ⅓ of the agarose gel. Under irradiation of ultraviolet ray (wavelength of 254 nm), photographs were taken, to determine the degradation degree of the RNA. The TAP sample purified by the method illustrated above contained almost no RNA-degrading activity under the condition.

EXAMPLE 3

Ultra-super Sensitive Assay Method of TAP Purity

So as to examine whether or not the purified TAP could cleave the cap structure of mRNA with no deterioration of the RNA chain, the following ultra-super sensitive assay method of TAP purity was established. Because the RNA to be treated with TAP in accordance with the present invention is mRNA with a cap structure at the 5'-terminus and with a polyA structure at the 3'-terminus, mRNA with the same structures at both the termini was prepared as a labeled form with two types of radioactive elements. Specifically, mRNA with the 5'-terminal cap structure labeled with tritium ($^3$H)-methyl ($CH_3$) group and with the RNA chain labeled with phosphoric acid containing radioactive phosphorus ($^{32}$P), was prepared, which was similar to intact mRNA from natural origin. The intact mRNA for use in the process according to the present invention can be expressed as follows.

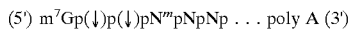

(5') $m^7Gp(↓)p(↓)pN'''pNpNp \ldots poly A$ (3')

wherein, m represents methyl group; p represents phosphate group; N represents four types of nucleotides; and G represents guanosine; and the downward arrow represents the site for TAP cleavage reaction.

Because the mRNA is labeled at the methyl group and phosphate group with trace amounts of radioactive elements with high specific activities, namely $^3$H and $^{32}$P, the desired cleavage of the cap structure, namely dissociation of m $^7$G (7-methyl guanosine) from the mRNA itself, and $^{32}$P-nucleotide derived from the "undesirable RNA degradation due to nuclease contamination", and dissociation of phosphoric acid containing $^{32}$P from mRNA itself due to "undesirable phosphatase contamination" can be sharply assayed.

"$^3$H-m$^7$G" and "$^{32}$P-nucleotide+phosphoric acid containing $^{32}$P" were assayed by allowing TAP to react with the double-labeled mRNA, adding cold 5% trichloroacetic acid to the resulting reaction mixture and centrifuging the mixture (10,000×G, 10 min) to separate the supernatant fraction ($^3$H-m$^7$G) from the precipitate fraction (mainly $^{32}$P-RNA and $^3$H-methyl derived from N''') and separately count $^3$H and $^{32}$P with a liquid scintillation counter (manufactured by Beckman, Co.).

The assay method using mRNA labeled with "$^3$H-methyl-$^{32}$-phosphoric acid" is ultra-super sensitive for the monitoring of contaminated nuclease; and simultaneously, the method can determine whether or not TAP practically cleaves the cap structure. The method provides an important marker as to the practical purity of TAP during purification for the invention.

The ideal assay results by the method are such that "50% of the tritium radioactivity of $^3$H-m$^7$G as the cleavage product of the cap structure transfers to the supernatant; and 100% of the $^{32}$P radioactivity in RNA remains in the precipitate fraction". Such ideal results could never be yielded when the TAP purified by us at the early stage or commercially available TAP products were used. As the consequence of the repetition of the aforementioned purification procedures, finally, we obtained a high-purity TAP sample at a level usable in accordance with the invention. The method for preparing radioactively double-labeled mRNA with "$^3$H-methyl-$^{32}$P-phosphoric acid" and the method for assaying the mRNA will be described below.

(3.1) Preparation of poly-A mRNA Radioactively Double-labeled with $^3$H-methyl-$^{32}$P-pU Vaccinia virus contains, in its virus particle, various enzymes synthesizing virus mRNA with a cap structure and poly-A. The virus synthesizes about 50 types of mRNAs. These mRNAs can be used as model mRNA, because the mRNAs are very similar structurally to mRNA in higher animals and plants including humans (S. J. Higgins and B. D. Hames, RNA Processing, A Practical Approach, Vol. 11, pp.35–65, (1994)). The virus particle was purified by a method comprising infecting vaccinia virus with HeLA cell and recovering the virus particle from the infected cell by using glycerin-density gradient ultra-centrifugation (Wei, C. M. and Moss, B., Proc. Natl. Acad, Sci., Vol. 72, PP. 318–322, (1975)).

$^{32}$P-labeled mRNA was recovered from the reaction of the purified virus particle (about 100 μg) in a 0.5 mL reaction solution containing 100 mM Tris-HCl, pH 8.0,12 mM MgCl$_2$, 4 mM ATP, 2 mM GTP, 2 mM CTP, 0.1 mM UTP, 100 μCi (α-$^{32}$P) UTP (specific activity; 3,000 Ci/mM), 1 mM S-adenosylmethionine, 30 mM β-mercaptoethanol, 280 U/mL RNasin and 0.5% NP-40 at 37° C. for 2 hours.

Similarly, $^3$H-methyl-labeled mRNA was recovered from the reaction of a replicate of the virus (about 100 μg) in a 0.5 mL reaction solution containing 120 mM Tris-HCl, pH 8.0,12 mM MgCl$_2$, 4 mM ATP, 2 mM GTP, 2 mM CTP, 2 mM UTP, 50 μCi $^3$H-S-adenosylmethionine (specific activity of 78 Ci/mM), 30 mM b-mercaptoethanol, 280 U/mL RNasin, and 0.5% NP-40 at 37° C. for 2 hours.

After these reactions, the individual reaction solutions were extracted in phenol; and the synthesized RNAs were subjected to Sephadex G-100 column chromatography and thereby separated from unreactive substrates. By affinity chromatography with oligotex (dT) 30, RNAs with poly-A were purified and isolated. The aforementioned two types of RNAs were used for the purity assay of TAP of a single type or in mixture.

(3.2) Highly Sensitive Assay Method of TAP Purity

In the course of purification, TAP was examined by the following method. Specifically, 1 μL of the purified TAP (300 units) was added to and incubated in a 20 μL reaction solution containing 1×TAP buffer, $^{32}$P-RNA (4,000 cpm; about 1 ng) or $^{32}$H-methyl-RNA (2,000 cpm, about 1 ng) at 37° C.; and then, the degradation of $^{32}$P-RNA or the cap cleavage (decapping) reaction in the $^3$H-methyl-RNA was assayed within a given period of time. After the reaction, 5 μg of tRNA was added to the reaction mixture, followed by addition of cold 5% trichloroacetic acid solution and centrifugation, to assay the radioactivities in the supernatant fraction and the precipitate fraction.

Additionally, a method for detecting a trace amount of a RNA strand with one nick inserted therein (RNA nick detection method) was carried out, by allowing $^{32}$P-mRNA to react with TAP and thereafter assaying the change of $^{32}$P-mRNA after the termination of the reaction, by utilizing the affinity of the 3'-terminal poly-A with the (dT) 30 region on the oligotex (dT) 30. The three types of assay methods described above are separately used in a dependent manner to the purification degree of the TAP enzyme; at the highest purification stage, a combination of the $^3$H-methyl RNA/TCA method and $^{32}$P-mRNA/nick detection method was used for the final determination as to whether or not the resulting TAP enzyme could be used for the second step of the process according to the present invention. The combination is the most highly ranked for such determination.

The data of examples using the two methods are shown in FIG. 2. FIG. 2 shows graphs depicting the results of the removal of the cap structure with the highly purified TAP without damage of the RNA chain; the ordinate represents the detected radioactivity in % and the abscissa represents time (minute). The enzyme used was highly purified TAP; and the substrate was the mRNA of vaccinia virus. Open circle represents the cap cleavage reaction of $^3$H-methyl-RNA and closed circle represents the nick activity assayed by using $^{32}$P-mRNA. At the early stage of the research works for the present invention, furthermore, it was concluded that the purified TAP enzyme could be used practically for the present invention. Thereafter, the simple method using rRNA of *Escherichia coli* was used generally for purity assay.

EXAMPLE 4

Designing of Oligoribonucleotide Sequence

Furthermore, an oligoribonucleotide sequence to be ligated to the complete 5'-terminus of mRNA cleaved with TAP was designed. Thus, the invention has been achieved.

An oligoribonucleotide sequence found in cDNA as rarely as possible and with a high specificity is essentially selected and attached. Therefore, then, a 10-mer sequence for use for the RAPD (random amplified polymorphic DNA; Nuc. Acids Res., Vol.18, pp.6531–6535 (1990)) was designed. The occurrence frequency of the designed sequence was then calculated and expressed in numerical figure, to weigh the sequence.

As such 10-mer sequence, the 48,502-bp nucleotide sequence of *Escherichia coli* λ phage was grouped per 10 bases. Because of the presence of the circular structure, sequences carrying a 6-base sequence recognizable by restriction enzymes were excluded from the resulting sequences; and then, sequences at a GC content of 50% and with 3'-terminal G or C were extracted. In such manner, 450 sequences of 10 bases were extracted, which carried sequences satisfying the conditions for use for RAPD.

By using the high-speed homology search function in the data base software GENETYX-MAC/CD Ver. 22.0.2, a homology search of the resulting 450 sequences of 10 bases was carried out with the data base of eucaryotic organism-derived sequences of 69,936,993 bp in total among the nucleotide sequences included in EMBL-GDB release 34.0 (1993); the total number of sequences completely matching with or differing by one base from one of the 10-mer sequences was defined as homolog score. Additionally, the biological organism as the search subject was an organism with the cap structure and polyA sequence.

A homolog score of for example 1,000 means that the total number of sequences completely matching with or differing by one base is 1,000 among the sequences of 69,936,993 bp in total. The program for use in the homolog score calculation is based on the Lipman-Pearson method (Lipman, D. J. and Pearson, W. R., Science, 227: pp.1435–1441, 1985).

Figure 3:
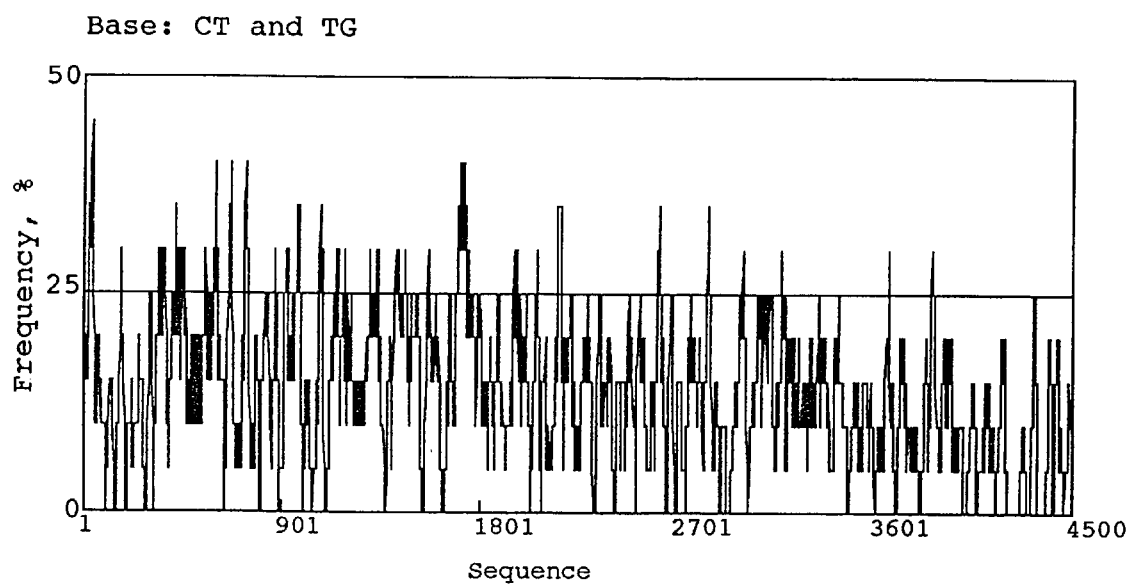
FIG. 3 shows bar graphs depicting the occurrence frequency of CT/TG dinucleotides vs. the homolog scores of 10-mer sequences.
Figure 4:
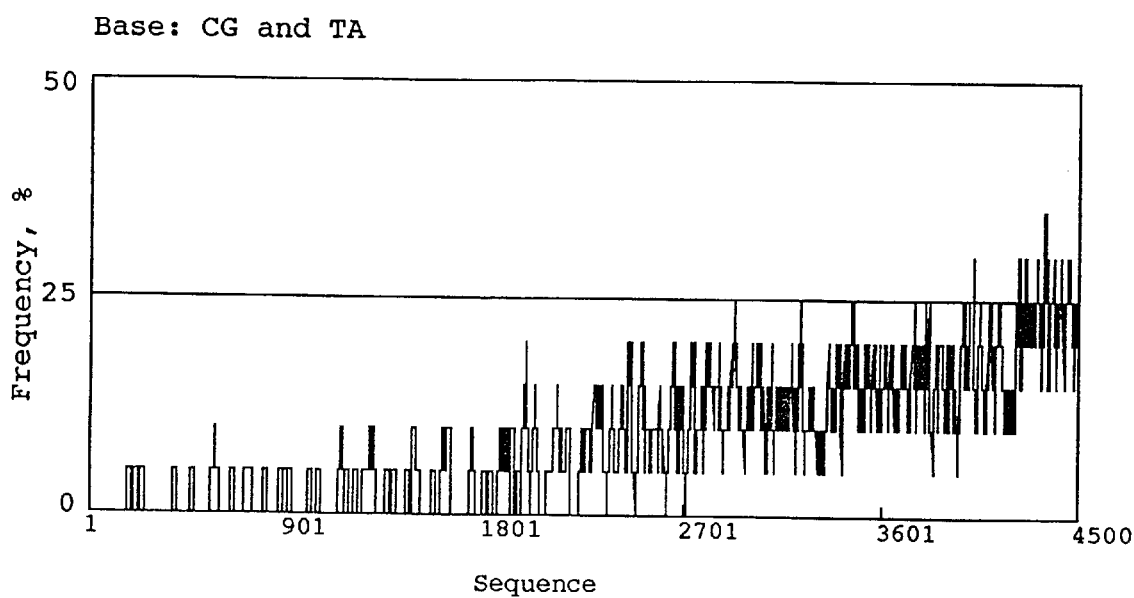
FIG. 4 shows bar graphs depicting the occurrence frequency of CG/TA dinucleotides vs. the homolog scores of 10-mer sequences.

In Tables 1 to 5 below, 450 homolog scores are aligned in the decreasing order of the score, where the score, primer and nucleotide sequence of each are shown. FIG. 3 shows an explanatory diagram depicting the occurrence frequency of CT/TG dinucleotides vs. the homolog score of 10-mer sequence. FIG. 4 shows an explanatory diagram depicting the occurrence frequency of CG/TA dinucleotides vs. the homolog score of 10-mer sequence. In FIGS. 3 and 4, the abscissa represents 450 sequences of 4,500 bases in the decreasing score order; and the ordinate represents dinucleotide occurrence frequencies plotted in %, namely the CT/TG occurrence frequency (FIG. 3) and the CG/TA occurrence frequency (FIG. 4), in 20-bp units by one-base shift along the left to right direction.

The frequencies of the dinucleotides in sequences with large homolog scores and sequences with small homolog scores were examined. Thus, it was confirmed that the rule of CT/TG excess and CG/TA deficiency was satisfactorily applicable (FIGS. 3 and 4). More specifically, a correlation was observed such that numerous CT/TG dinucleotides emerged in sequences with large homolog scores and the occurrence frequency of CG/TA dinucleotides was high in sequences with small homolog scores.

The following sequences are set forth in Tables 1 to 5:

SEQ ID NOS. 19 TO 108 for the sequences set forth in Table 1;

SEQ ID NOS. 109 to 198 for the sequences set forth in Table 2;

SEQ ID. NOS. 199 to 288 for the sequences set forth in Table 3;

SEQ ID NOS. 289 to 378 for the sequences set forth in Table 4; and

SEQ ID NOS. 379 to 468 for the sequences set forth in Table 5.

TABLE 1

| Scores | Primers | Nucleotide sequences | Scores | Primers | Nucleotide sequences |
|---|---|---|---|---|---|
| 7,786 | A-34 | CTGGAGAAAC | 4,128 | D-41 | CCTGTTTCTC |
| 6,165 | F-29 | TCTGAAGAGG | 4,126 | B-07 | TCAGCAACTG |
| 5,852 | E-22 | TTTCTCCTGC | 4,121 | B-36 | CCGAAAGAAG |
| 5,849 | D-48 | TGCTGGAAAG | 4,093 | A-05 | GAGGTGAATG |
| 5,611 | C-24 | TGCGGGAAAC | 4,052 | H-25 | GTCATCAAGC |
| 5,603 | F-47 | AGGGAAAAGG | 4,047 | D-03 | TGTTTTCCCC |
| 5,599 | A-19 | ACTGCTGAAG | 4,041 | H-10 | ATTTCTGCCC |
| 5,516 | A-32 | AACAGAGGAG | 4,039 | H-19 | CAGCTCTTTC |
| 5,341 | X-34 | ATCCTCTTCC | 4,020 | E-13 | AAACCACAGC |
| 5,316 | F-03 | ACATCAGCAG | 4,019 | H-40 | CACTCTTCTC |
| 5,310 | A-33 | GAGAAGAGTG | 3,995 | B-48 | CTTTCTGTCC |
| 5,185 | F-05 | GAGAAACAGG | 3,972 | X-40 | CGAAAACCAG |
| 5,145 | B-10 | ACTGAGGATG | 3,958 | G-01 | CTGCTTTTCC |
| 5,080 | G-25 | ACAAAGGAGG | 3,951 | B-23 | GAATGAAGCC |
| 5,059 | B-40 | AGGAAGACAG | 3,943 | C-13 | TTGCTGAGTG |
| 5,028 | F-33 | GACAAGGATG | 3,915 | B-22 | GTTTCTGGTG |
| 4,939 | A-16 | TGAGGAAAGC | 3,903 | C-37 | GACCAAAGAC |
| 4,914 | D-49 | TTCTGCTTCC | 3,890 | E-42 | ATTCCTGTGG |
| 4,681 | C-33 | GGAAAAGCAG | 3,888 | D-35 | GAGACACAAC |
| 4,638 | G-28 | GGACAGAAAG | 3,879 | F-01 | CCCAAAACAC |
| 4,567 | D-50 | AGACCATCTC | 3,856 | D-42 | GTGTTTGTGC |
| 4,537 | E-26 | GTGACAGAAG | 3,840 | E-31 | TTTGCTCCAG |
| 4,532 | H-39 | GTTTCTCCAG | 3,839 | A-21 | CTGATGACAG |
| 4,522 | E-07 | ACAACAAGGC | 3,831 | H-31 | TTCAGAGGTG |
| 4,497 | B-20 | GTGGTGAAAG | 3,831 | C-01 | AAAGGTGAGC |
| 4,496 | E-04 | TTCCTTTCCC | 3,826 | D-45 | ATCACACACC |
| 4,470 | H-21 | TTTCCTCACC | 3,807 | H-34 | GAATGCCAAC |
| 4,447 | E-46 | ACCACCAAAG | 3,800 | C-49 | CAGTGATGAC |
| 4,445 | E-27 | AATCCAGCAG | 3,793 | C-04 | GTGACTTCTG |
| 4,428 | B-09 | GAAAGAGCTG | 3,792 | C-14 | TGCTGAACAG |
| 4,414 | B-49 | TTCTGTGGAC | 3,789 | F-10 | GTTTCAGGAG |
| 4,394 | E-49 | AAAAGGCAGG | 3,788 | G-50 | TGTCATCAGC |
| 4,388 | H-06 | CACCAGAAAC | 3,786 | E-40 | ACACAGGAAC |
| 4,351 | C-22 | TGAGGTGAAC | 3,775 | H-47 | TCATCTGCTC |

TABLE 1-continued

| Scores | Primers | Nucleotide sequences | Scores | Primers | Nucleotide sequences |
|---|---|---|---|---|---|
| 4,345 | D-29 | CTCCTGAAAC | 3,775 | B-35 | AAAGCAGACG |
| 4,317 | C-11 | TTCTCAGGAG | 3,756 | F-17 | AAGTCAGAGG |
| 4,301 | B-27 | CCTGAAACTG | 3,745 | H-23 | CAAATGCCAC |
| 4,279 | D-07 | ATCTGGGAAC | 3,712 | A-26 | TGAGAGTGAG |
| 4,274 | A-22 | CAGAAAGACG | 3,709 | B-47 | AATGCCAACC |
| 4,256 | E-45 | ACTCCTTCAG | 3,689 | B-17 | TGTGGAGTTC |
| 4,256 | C-34 | TGAAACCAGC | 3,685 | C-28 | CAGAAGTCAC |
| 4,246 | C-45 | TGTCTTTGCC | 3,659 | H-38 | TTTTCTGCCG |
| 4,229 | E-48 | CAATGCTGAG | 3,656 | G-46 | AATCTGCTCC |
| 4,223 | E-02 | TGAGAGATGG | 3,642 | G-35 | ATCCAGTTCC |
| 4,211 | A-06 | TGGTGAAGTC | 3,641 | F-04 | GCACAAACAC |

TABLE 2

| Scores | Primers | Nucleotide sequences | Scores | Primers | Nucleotide sequences |
|---|---|---|---|---|---|
| 3,638 | E-09 | TCACACCAAC | 3,232 | H-05 | GGCTTCATTC |
| 3,636 | X-29 | CGTCTTTCTG | 3,227 | D-02 | TCAAACAGGG |
| 3,631 | X-32 | CTGTCATCAG | 3,215 | A-14 | AAACACCACG |
| 3,611 | H-08 | CTTTCACCAC | 3,212 | F-07 | GTTGTGTCTC |
| 3,807 | B-33 | TGATGACCAG | 3,209 | G-08 | AATCAGCCAC |
| 3,603 | E-25 | GCAAATGGTG | 3,208 | E-01 | CTCAGCATTG |
| 3,583 | D-47 | GTGTTTTGGG | 3,208 | B-11 | ACTGAACTCC |
| 3,570 | E-18 | CTTCTGTCAC | 3,186 | X-35 | ACTGAGATCC |
| 3,567 | D-33 | ATGGCTGAAC | 3,174 | H-36 | TCTTTGCTCG |
| 3,563 | E-47 | ACAAGGTCAC | 3,169 | C-16 | AGGGCAAAAC |
| 3,561 | F-24 | GAGCAGATTG | 3,164 | A-49 | TGAACTGGTC |
| 3,552 | F-40 | GTCATCACTG | 3,161 | X-03 | CTTTCTACCC |
| 3,542 | B-14 | GATTCAGAGC | 3,154 | G-15 | TAAGCCATCC |
| 3,530 | H-42 | TCAGACCATC | 3,144 | A-12 | CTGGTTTTCG |
| 3,525 | F-12 | GATTCAGAGG | 3,095 | G-06 | TTGCCACTTC |
| 3,518 | A-03 | AATGCCAGAG | 3,084 | C-07 | TTGTTCCCAG |
| 3,518 | A-02 | GGAACTGAAG | 3,077 | C-27 | GTGAATGGTG |
| 3,508 | C-06 | GAAACTGAGC | 3,070 | X-02 | TGGATTGGTC |
| 3,501 | C-32 | TCTGGTTCTC | 3,070 | C-44 | ACAGAGGTTC |
| 3,491 | B-05 | AAAAAGGGGC | 3,059 | G-38 | CCACAAATCC |
| 3,480 | H-20 | ACCAGTTTCC | 3,058 | D-43 | AGTCCTGAAC |
| 3,477 | E-16 | CATCAACCAG | 3,047 | B-44 | GGTGAGTTTG |
| 3,456 | G-19 | GCTCAGTTTC | 3,046 | F-35 | ACTGACACAG |
| 3,448 | D-21 | TGGATGAACG | 3,038 | A-44 | GTGAGTTCAC |
| 3,438 | C-09 | TTTCTCTCGG | 3,035 | E-23 | TCTGGTTTCG |
| 3,433 | H-16 | GCTCTGAATC | 3,033 | D-04 | TTTGTGCCAC |
| 3,424 | H-32 | ACTTTCTCCG | 3,024 | H-28 | GTGAACTCAC |
| 3,414 | H-24 | TTCACCAGTG | 3,018 | F-11 | AACACATCCG |
| 3,388 | G-30 | CTGCTCAAAC | 3,015 | X-14 | GTACAAGTCC |
| 3,386 | A-42 | ATTGCTCAGG | 2,976 | G-13 | AGGTGGTTTC |
| 3,360 | G-33 | AGTTCTGCTC | 2,969 | E-41 | AGCCATTCTG |
| 3,342 | H-01 | CGGAAAAGTC | 2,966 | B-41 | GGATTTGTGG |
| 3,329 | X-04 | TTTTGGCTCC | 2,965 | A-35 | TGAACACACC |
| 3,317 | H-02 | CAGTTTCAGG | 2,964 | D-11 | AAGAGTGGTG |
| 3,314 | F-49 | GTCTTTGGTC | 2,960 | X-46 | CATTCACCTC |
| 3,304 | C-36 | GAAAGAGTGG | 2,957 | A-17 | TGGCTGATTG |
| 3,296 | A-46 | GGTGAACAAC | 2,944 | F-50 | CCACTCTTTC |
| 3,289 | X-18 | GATCTCAGAC | 2,938 | G-48 | TGAACTGTGC |
| 3,284 | B-18 | CTACAATGCC | 2,932 | A-47 | GCTTGATGAC |
| 3,284 | A-27 | CGTGTTTGAG | 2,910 | A-50 | GTGGCATTTG |
| 3,276 | D-28 | CCTCTGAATC | 2,908 | G-20 | TGCTCAGTTG |
| 3,269 | G-31 | CAAACTCACC | 2,906 | X-41 | GGATTCACTG |
| 3,268 | B-03 | TCCCTGTTTG | 2,894 | F-38 | TGAAATGCCC |
| 3,256 | H-44 | AACATCTGGC | 2,883 | D-32 | AAACAGGTGC |
| 3,250 | X-50 | CTTCAGTTCC | 2,878 | G-07 | CGCTGAAATC |

TABLE 3

| Scores | Primers | Nucleotide sequences | Scores | Primers | Nucleotide sequences |
|---|---|---|---|---|---|
| 2,874 | F-13 | CTGATTCAGG | 2,494 | G-42 | ATTTCAGCCG |
| 2,863 | D-40 | TGGTTTTGCG | 2,485 | H43 | CTATCCAGTC |
| 2,857 | B-45 | GTTTGAGCAG | 2,480 | F-36 | TGAGGTTTGC |

TABLE 3-continued

| Scores | Primers | Nucleotide sequences | Scores | Primers | Nucleotide sequences |
|---|---|---|---|---|---|
| 2,854 | F-22 | AAAGTGCCAC | 2,478 | A-45 | GATGAGTTCG |
| 2,846 | D-44 | ACATTGGCAG | 2,474 | A-15 | CTTACCTGAC |
| 2,828 | G-43 | CTTCTTTCGG | 2,451 | H-26 | GTTGTTCACC |
| 2,827 | E-19 | CACCATTTGC | 2,444 | E-34 | ATACACCCAC |
| 2,825 | X-24 | GATCATGGTC | 2,442 | B-42 | GTATCAGGAG |
| 2,808 | G-37 | CTCCTGATAC | 2,433 | B-21 | CAGTGGTATG |
| 2,798 | B-28 | CACTTTTCCG | 2,425 | D-27 | CCTGAATCAG |
| 2,795 | D-08 | CATCCTTGTC | 2,410 | C-46 | TGACAGTCAC |
| 2,791 | G-05 | CACCATTCAC | 2,409 | A-29 | GACTGGATAG |
| 2,770 | H-22 | GTAATGGTGG | 2,405 | E-36 | TTTGTCACCG |
| 2,770 | C-39 | AGCCAGTTTC | 2,384 | E-14 | AATGGTCTGC |
| 2,762 | C-19 | ACAGTGCTAC | 2,364 | H-49 | AAAAGACCCG |
| 2,761 | D-15 | CAATCTGCTC | 2,325 | X-08 | TGGTAAAGGG |
| 2,742 | A-25 | AATGACAGCG | 2,323 | A-37 | CATTACCAGC |
| 2,726 | X-30 | TACTGTTGCC | 2,321 | X-17 | GATCTGACAC |
| 2,721 | C-31 | GGAACTACAG | 2,321 | F-48 | TTCATTCCCG |
| 2,718 | B-50 | TGAACAGGTG | 2,314 | G-09 | CATTACTGCG |
| 2,712 | X-42 | ACTTTTGGCG | 2,312 | A-40 | CTACAAGTCC |
| 2,699 | H-48 | ATTTCTGCGG | 2,308 | H-07 | CATACCACTG |
| 2,684 | E-08 | TCAACATCGC | 2,292 | G-12 | TCACCCTTTG |
| 2,661 | E-29 | AGCACAATGG | 2,283 | C-04 | TTTGAGCACG |
| 2,656 | X-05 | GGAACCAATC | 2,276 | F-16 | AAACCTGTCG |
| 2,649 | E-24 | TGCCTCATTG | 2,273 | X-15 | GTACCAGTAC |
| 2,649 | B-04 | TCTTGAGCAG | 2,253 | G-17 | GACAATCTGG |
| 2,648 | E-35 | AAAGGCATCG | 2,253 | E-44 | GCTGTATCAG |
| 2,644 | C-38 | AGGCAAACTG | 2,241 | C-29 | CGTGAGTTTC |
| 2,628 | H-46 | CTCAAACACG | 2,235 | C-10 | TGCCAGTATG |
| 2,628 | H-13 | ACCTTTCACC | 2,232 | H-14 | GGCATTGTAG |
| 2,615 | C-03 | GAAACTCACG | 2,231 | X-38 | GTCAGGTAAG |
| 2,612 | C-25 | GATTTCAGCG | 2,223 | D-13 | GCAAGTGTAG |
| 2,612 | A-39 | GTTGGCATTC | 2,213 | B-34 | GTCCTGATAC |
| 2,606 | E-50 | TTTTCTGCGG | 2,210 | H-03 | CATACCAGAC |
| 2,585 | X-23 | CATCTGACTG | 2,173 | D-14 | TTTCACACCG |
| 2,571 | C-23 | TTGGCTGTAC | 2,170 | X-12 | CTGCTTGATG |
| 2,571 | A-09 | CCGTGAAAAG | 2,168 | X-39 | GACAATCTGC |
| 2,570 | A-13 | GCAGATTGTC | 2,168 | H-27 | CGAACTCATC |
| 2,559 | D-38 | TTGCAGGTTG | 2,165 | X-01 | TACAACGAGG |
| 2,551 | C-08 | CCAGATTGTC | 2,152 | G-44 | GTATCAGGAC |
| 2,548 | E-30 | CTGGTTGATG | 2,143 | F-09 | GCGTTTGATG |
| 2,530 | B-02 | CCACCATTAC | 2,134 | H-35 | GCTGGTAATG |
| 2,510 | E-20 | AGTGACATCG | 2,130 | C-02 | CAGTATCAGC |
| 2,506 | G-22 | AATCTCACCC | 2,127 | H-18 | GAAAATCCGC |

TABLE 4

| Scores | Primers | Nucleotide sequences | Scores | Primers | Nucleotide sequences |
|---|---|---|---|---|---|
| 2,109 | A-10 | CAGTGAATCC | 1,692 | E-06 | GTAAACTCCG |
| 2,104 | G-21 | TGAAAGTCCG | 1,689 | A-20 | GTGCCTTATC |
| 2,095 | A-11 | AAATGGACGC | 1,684 | F-28 | ACCCTATCTC |
| 2,089 | X-37 | AGCAGATACG | 1,622 | G-40 | TGTAATCCGC |
| 2,084 | D-24 | TTATCCCCTG | 1,615 | F-10 | CACTAACACC |
| 2,066 | B-15 | CAGTATGGTG | 1,614 | F-45 | CCACTATCTG |
| 2,033 | B-31 | TCAGATTGCG | 1,611 | A-23 | GGAGTTTACG |
| 2,031 | F-44 | GCTTACTTCC | 1,609 | F-27 | GTGCTTTACG |
| 2,017 | D-25 | CACTAAAGGG | 1,608 | H-15 | CACCATACTG |
| 2,005 | D-46 | GCTCAGTATC | 1,595 | A-30 | GAAACGATGG |
| 1,990 | C-50 | TATGTGAGCG | 1,594 | E-33 | ATTTGGTCGG |
| 1,987 | D-26 | TCGCATCAAC | 1,588 | C-41 | CAGATAGTGG |
| 1,976 | F-02 | GATACTGAGC | 1,574 | B-24 | AGTGCTTACC |
| 1,965 | F-26 | CTACACTTGC | 1,566 | F-20 | CACGGAAATG |
| 1,961 | B-26 | GTCTGGTATG | 1,531 | F-23 | TTCGGTGATG |
| 1,946 | B-12 | GCGGATTTTC | 1,521 | X-33 | GATAAGGCAC |
| 1,935 | F-39 | GTTTACCTCC | 1,517 | G-02 | CTGTAGTTCC |
| 1,924 | C-15 | AGGGGAATAC | 1,516 | H-04 | CCACGTTTTC |
| 1,914 | E-05 | CTGATACAGC | 1,500 | C-12 | TGATTGGTCG |
| 1,913 | D-30 | CATCAAACGC | 1,493 | E-39 | GGTGTTAGTG |
| 1,913 | C-35 | ATTCGTGGAG | 1,490 | H-29 | CATCGTGTTG |
| 1,899 | X-43 | CTTTTCACGG | 1,486 | X-28 | CGTAAACTCC |
| 1,897 | D-12 | CGTAAAGCAC | 1,486 | F-14 | CCCTTTAGTG |
| 1,893 | D-01 | GGAGGTAAAC | 1,480 | C-21 | CGCAGTAATG |
| 1,889 | E-43 | CGGAGTTTAC | 1,476 | F-18 | GCAGATTACG |

TABLE 4-continued

| Scores | Primers | Nucleotide sequences | Scores | Primers | Nucleotide sequences |
|---|---|---|---|---|---|
| 1,835 | H-30 | ACTTGTCACG | 1,472 | X-36 | CCCGTTTTTG |
| 1,827 | C-05 | AACGAGAGAG | 1,455 | B-30 | CAAAACGCTG |
| 1,825 | X-49 | TGACTGTTCG | 1,447 | D-37 | GCTCAATACG |
| 1,825 | D-16 | CCCCTATTTG | 1,440 | G-16 | TTCGCTGATG |
| 1,821 | B-16 | ATGACTACCG | 1,424 | X-48 | TTAGCATCCG |
| 1,820 | G-39 | ACTGTTTCGG | 1,419 | H-17 | TATCGCTGTC |
| 1,816 | F-37 | TGACGGCAAC | 1,418 | H-50 | ACGGGTAAAG |
| 1,814 | G-14 | AGGTAAAGCG | 1,418 | D-23 | TACACCGAAC |
| 1,811 | B-46 | GGCTATTCTC | 1,406 | G-29 | GAGAATAGCC |
| 1,792 | B-25 | GAAAACGTGG | 1,403 | A-08 | ACTAATGGGC |
| 1,772 | A-28 | TTTATGGGGC | 1,390 | G-23 | AATAGCCTCC |
| 1,760 | F-19 | TAGTTGCCTG | 1,374 | F-08 | CCTAATCAGC |
| 1,746 | F-32 | TCGGATTTGC | 1,372 | X-27 | GTGATAACCG |
| 1,743 | D-18 | AGTGGGTTAC | 1,371 | X-26 | GATCTAAGGC |
| 1,737 | G-26 | GCTGATACTG | 1,357 | B-19 | GAGTCCTATG |
| 1,735 | H-09 | TTTCACCGTG | 1,354 | X-06 | AAACTCCGTC |
| 1,725 | H-33 | GGACTTGTAG | 1,354 | F-06 | CGTATTGAGC |
| 1,711 | D-05 | TCTGACGATG | 1,352 | H-12 | AGTCAACGTC |
| 1,701 | A-18 | CAAAAACGGG | 1,340 | D-34 | GCTGATTAGG |
| 1,699 | A-36 | AGTGTAAGGG | 1,339 | F-21 | CAAATAGGGG |

TABLE 5

| Scores | Primers | Nucleotide sequences | Scores | Primers | Nucleotide sequences |
|---|---|---|---|---|---|
| 1,338 | B-01 | AGCCGAAATG | 1,023 | X-44 | TGTTATCCCG |
| 1,337 | C-48 | CGTTATGAGC | 1,001 | X-13 | GTTTTCGCAG |
| 1,327 | X-19 | GATCATAGCC | 987 | E-32 | ATTCGCAGTG |
| 1,319 | F-46 | TTTTTCCGCC | 979 | E-37 | GAACGGATAC |
| 1,319 | D-22 | CGTAATCTGC | 979 | A-48 | ACCGTGATTC |
| 1,312 | A-04 | ACTGATACCG | 973 | D-10 | GCGGTAAATC |
| 1,305 | A-41 | TTTCTGCGTC | 956 | A-01 | CTGTCGTTTC |
| 1,304 | D-17 | CATTTCCGTG | 955 | A-07 | CCGACTATTC |
| 1,304 | C-20 | CAGCGATTTC | 952 | X-21 | GATCTAACCG |
| 1,302 | A-24 | CGGTTATCAC | 951 | B-13 | AATACACGGG |
| 1,292 | G-10 | GAAATCGCTG | 948 | D-09 | CATCCGTTTG |
| 1,291 | B-08 | TATTGAGCGG | 930 | D-06 | CACGAATGTC |
| 1,281 | C-43 | ATGAACGGTG | 917 | E-03 | ACCGTTGTTC |
| 1,251 | B-39 | ATGAAGCGAC | 883 | A-31 | TGCGACAATC |
| 1,249 | X-10 | GGTACTAAGG | 872 | X-09 | TCGGTCATAG |
| 1,249 | A-38 | AGTGCGAAAG | 839 | B-06 | AGCGTTCATC |
| 1,246 | H-11 | CATAGGACTC | 822 | B-37 | AGAGCGATAC |
| 1,238 | G-11 | GTATGACGAC | 821 | E-28 | GTAACGCAAC |
| 1,236 | G-47 | CAGCGTTTTG | 805 | G-24 | ATAACCGCAC |
| 1,228 | X-07 | TCGATACAGG | 799 | X-31 | ACCCGTTTAC |
| 1,228 | F-30 | GATTTACCGC | 791 | X-16 | GATCACGTAC |
| 1,205 | C-42 | GGAAGTAAGC | 784 | H-37 | ACGGTCATAC |
| 1,193 | G-27 | TTCGTTCTGC | 765 | D-19 | TATTGACGCC |
| 1,180 | A-43 | CAACACGATG | 765 | C-18 | GTCGTCATAC |
| 1,179 | F-31 | CAAACGGATG | 762 | E-38 | CAATAGCGAC |
| 1,179 | E-15 | TTACGCTGTG | 754 | G-18 | AATACGCCAC |
| 1,175 | H-45 | TGCTCATACG | 745 | C-47 | GTTTACGGTG |
| 1,162 | B-32 | GCGTATGTTG | 744 | D-39 | TCTACTCGTG |
| 1,158 | X-20 | GATCAATCGC | 730 | C-30 | TGACCGTAAC |
| 1,143 | D-31 | ACGGGTAATG | 718 | B-43 | GATTTACGCG |
| 1,128 | B-29 | AAAGTCCGTG | 713 | E-12 | GTATCCGTTC |
| 1,124 | D-36 | TGTTATGCCG | 709 | F-15 | ACATACGAGC |
| 1,117 | X-47 | ACGGATGTAG | 696 | F-42 | CACCGTAAAC |
| 1,109 | C-17 | AAACGCTCTG | 694 | G-41 | GTTCGTAAGC |
| 1,097 | H-41 | CCATCGTTTC | 693 | C-03 | TCCGTATGTC |
| 1,090 | G-49 | AAATGACGCC | 680 | G-34 | TGCGACATAC |
| 1,083 | G-36 | ATCGCCATAC | 677 | G-32 | CCCGTAAATC |
| 1,082 | F-43 | TAAAACGCCC | 673 | E-11 | GTCGCTATTG |
| 1,078 | F-34 | GACATTCGTG | 640 | E-21 | TGATTAGCGG |
| 1,076 | F-41 | GCTCATAACG | 634 | C-40 | TGACGATAGC |
| 1,070 | G-45 | CAACATACGC | 616 | B-38 | GCTTACGAAC |
| 1,066 | X-25 | GATCATAGCG | 609 | X-45 | GAATAGTCGG |
| 1,062 | X-22 | GATCGCATTG | 581 | E-17 | GTTGCGTTAC |
| 1,059 | D-20 | ACCAAACGAC | 551 | C-26 | ACAGCGTATG |
| 1,048 | X-11 | TACCTAAGCG | 526 | F-25 | ATGCGTAAGG |

For the purpose of confirming the analysis results, the resulting 450 sequences were used for the RAPD analysis using human genome- or mouse genome DNA; depending on the amplification degree of PCR products and the number of ladder (complexity), sorting was performed; among them, several sequences with lower amplification degrees and less ladder patterns (group 1 and several sequences with higher amplification degrees (group 2 ) were selected for PCR. FIG. 5 shows an explanatory diagram depicting the RAPD analysis results of the selected primers of 10-mer sequence and human genome DNA as template vs. the homolog scores. More specifically, all the 450 sequences of 10-mer were subjected to RAPD analysis and classification, depending on the basis of the difference in pattern. From 10mer sequences with less RAPD patterns (group 1; FIG. 5a) and 10-mer sequences with more RAPD patterns (group 2; FIG. 5b) were sampled several sequences, for additional RAPD.

Consequently, as almost expected but with some exception, a correlation in the amplified PCR product pattern was observed between the group of the primers with large homolog scores and the group of the primers with small homolog scores, when used (FIGS. 5a and 5b). The total score of each of the groups is shown, and apparent difference is observed.

The results indicate that such analysis is meaningful even if the sequences registered in the data base used were biased severely and that such analysis provides efficacious information for the analysis of enormous genes, such as genome analysis.

Based on the aforementioned results, an oligoribonucleotide was designed from the following two standpoints.

Firstly, a sequence of a small homolog score is referenced because a sequence of a smaller homolog score is estimated to be at a low occurrence frequency of the sequence on genome.

Secondly, the ligation efficiency of a DNA fragment treated with a restriction enzyme forming a blunt end is known to below. Thus, it was deduced that the ligation efficiency of the end of an oligoribonucleotide to the 5'-terminus of TAP-treated mRNA would vary, depending on the end.

From the two standpoints, 7 oligoribonucleotides were prepared. FIG. 6 shows the prepared 7 oligoribonucleotides, compared with the sequence of vectorette (Nuc. Acids. Res., Vol.18, pp.2887–2890 (1990)). In the figure, the title of 10-mer sequence is shown in parenthesis underneath each of the sequences. Additionally, the sequences of the oligoribonucleotides of 8 in total, as shown in FIG. 6, are listed as SQ ID Nos. 1 to 8 in the sequence listing table. Herein, the individual oligoribonucleotides were synthesized and purified by HPLC (Nippon Gene Co., Ltd. Custom Synthesis Service).

The first 7 oligonucleotides are composed of the entirety or a part of a series of sequences with small homolog scores shown in Table 5. For example, the oligoribonucleotide "GG" is composed of a series of three 10-base sequences (E-17, C-26, F-25; T is modified into U) with the smallest homolog score.

EXAMPLE 5

Synthesis of Human Placenta 5' cDNA and Analysis of 5'-terminus of Human Placenta Lactogen mRNA The sequence of the 5'-terminus of mRNA of for example human placenta lactogen was analyzed. Human placenta immediately after delivery was frozen as soon as possible and was then used as a starting material for RNA extraction. The frozen placenta was immersed in liquid nitrogen and finely disrupted so as to avoid the thawing thereof under caution; the resulting placenta was placed, as it was frozen, in a guanidine thiocyanate solution and solubilized with Polytron homogenizer, from which the total RNA was extracted. From the total RNA was extracted polyA+ RNA on oligodT cellulose (Gibco BRL Co.).

In a typical example, the total RNA can be recovered at a yield of 2.5 mg from 10 g of human placenta issue; poly-A$^+$RNA can be extracted at a yield of 0.06 mg from the total RNA of 6 mg. For more additional description, the separation method of RNA is not limited to the method herein listed; for example, the method is described in detail in Method. In Enz. Vol. 152 (1987 ), Academic Press.

As described below, human placenta 5'-cDNA was synthesized.

Step 1: Dephosphorylation of 5'-terminus of Non-full-length mRNA

A reaction volume of 100 μL containing 5 pg of human placenta poly-A $^+$RNA, 0.1 M Tris-HCl, 10 mM DDT, pH 7.6,160 U RNasin (Promega Co.), and 10 U alkali phosphatase (CIAP, Nippon Gene Co., Ltd.) was prepared and kept warm at 37° C. for 30 minutes. For the purpose of protein denaturation in the solution to inactivate alkali phosphatase and purify RNA, phenol treatment once, chloroform treatment once and ethanol precipitation once were carried out. After the reaction, the resulting solution was dissolved in 50 ∞L of $H_2O$ treated with diethylpyrocarbonate (referred to as DEPC-$H_2O$ hereinafter) after reaction.

Step 2: TAP Treatment

To 50 μL of the solution containing RNA after CIAP treatment were added 10×TAP buffer (500 mM sodium acetate, pH 5.5, 50 mM EDTA, 100 mM β-ME), 160 U RNasin, and 300 U TAP; by using DEPC-$H_2O$, the resulting solution was adjusted to a final reaction volume of 100 μL, for reaction at 37° C. for one hour. Through phenol treatment once, chloroform treatment once, and ethanol precipitation once, the resulting reaction mixture was dissolved in 33.5 μL of DEPC-$H_2O$.

Step 3: Oligoribonucleotide Ligation with T4 RNA Ligase

10 μg of an oligoribonucleotide (AA described in Example 2 was used herein; AA: GUUGCGUUACACA GCGUAUGAUGCGUAA), 10×T4 RNA ligase buffer (500 mM Tris-HCl, 100 mM $MgCl_2$, 10 mM β-ME, 10 mM ATP), 0.5 μL of 100 mM ATP, 160 U RNasin, and 250 U T4 RNA ligase (New England Biolab. Inc.) were added to and thoroughly mixed with 33.5 μL of the CIAP/TAP-treated RNA prepared at the step 2 to a final reaction volume of 50 μL; then, 50 μL of 50% polyethylene glycol 6000 (PEG 6000) was added to the reaction mixture to a final PEG concentration of 25%; and the resulting mixture was kept warm at 20° C. for 16 hours.

So as to decrease the viscosity due to PEG after the termination of the reaction, 200 μL of DEPC-$H_2O$ was added to the reaction mixture, followed by thorough agitation to decrease the viscosity. Subsequently, phenol treatment once and chloroform treatment once were carried out. Then, 1 μL of Ethachinmate (Nippon Gene Co., Ltd.) and 30 μL of 3M sodium acetate were added to the resulting solution, followed by blending and subsequent ethanol precipitation. The precipitate was recovered and dried, which was then dissolved in 100 μL of DEPC-$H_2O$, followed by addition of 50 μL of ammonium acetate for ethanol precipitation. The ethanol precipitation procedure was repeated three times. Finally, the resulting ethanol precipitate was dried and dissolved in 50 μL of DEPC-$H_2O$, which was defined as oligo capping purified RNA, in which the oligonucleotide was replaced for the cap structure.

Step 4: Synthesis of First-strand cDNA

To 50 μL of the oligo capping RNA as template was added 5 μL of 20 μM random hexamer; and the resulting total volume of 55 μL was kept warm at 70° C. for 10 minutes and then cooled on ice; to the resulting solution were immediately thereafter added 20 μL of 5×First-strand buffer (manufactured by Gibco BRL, Co.), 10 μL of 0.1 M DTT, 20 μM dNTP mixture solution, and 5 μL of RNasin to a final volume of 95 μL, which was kept warm at 37° C. for 2 minutes; immediately thereafter, 5 μL (1,000 U) of Superscript II (manufactured by Gibco BRL, Co.) was added to the resulting mixture, for 30-min reaction at 37° C. After the reaction, the mixture was kept warm at 95° C. for 10 minutes to inactive the enzyme, followed by addition of 400 μL of DEPC-$H_2O$, to prepare 500 μL of human placenta oligo capping cDNA.

The human placenta oligo capping cDNA thus prepared was examined by analyzing the sequence of the 5'-terminus of the mRNA of placenta lactogen.

Human placenta lactogen, a peptide hormone belonging to the growth hormone gene family and of a molecular weight of 22 kDa, forms a cluster on the human chromosome 17. The expression mode and the like are now researched progressively (Genomics, 4(4): pp.479–497 (1989)). As to human placenta lactogen, additionally, it has already been reported that transcription products with different transcription starts are present in the placenta (Biochem. Int. 16 (2) pp.287–292 (1988)).

Step 5: Synthesis of Second-strand cDNA

Using a gene-specific primer ASP1:

(5'-GTTGGAGGGTGTCGGAATAGAGTC-3')

prepared from the placenta lactogen gene and an AA oligo-specffic primer RC5':

(5'-GCGTTACACAGCGTATGATGCGT-3')

comprising a partial sequence within the AA oligo, PCR was carried out. The sequences of the primers ASP1 and RC5' are shown as SQ ID Nos. 9 and 10, respectively, in the attached sequence listing table. More specifically, 1 μL of human placenta oligo capping cDNA, 5 μL of 10×GeneTaq buffer (Trademark; manufactured by Nippon Gene Co., Ltd.), 5 μL of 2.5 mM dNTP mixture solution, 2 μL each of ASP1 and RC5' (each at 25 μM) and 2.5 U GeneTaq (Trademark; manufactured by Nippon Gene Co., Ltd.) in mixture of a final reaction volume of 50 μL were subjected to the following PCR; one round of 95° C. for 5 minutes, 35 cycles of 94° C. for 30 seconds, 55° C. for 30 seconds and 72° C. for 60 seconds and a final round of 72° C. for 5 minutes.

5 μL of the resulting PCR product was subjected to 1.2% agarose electrophoresis; the PCR product was detected at an expected size and considered to be derived from the 5'-terminus of human placenta lactogen mRNA. Using T4 RNA polymerase, the PCR product was blunt ended and subcloned in plasmid pUC19 preliminarily treated by digestion with a restriction endonuclease SmaI and subsequent dephosphorylation, for the determination of the nucleotide sequence. Consequently, it was verified that the resulting 5'-terminal sequence of the human placenta lactogen mRNA coincided with the sequence reported in Genomics, 4(4): pp.479–497 (1989) and in Biochem. Int., 16 (2): pp.287–292 (1988).

Figure 7:
FIG. 7 shows an explanatory diagram depicting the 5'-terminal analysis results of human placenta lactogen mRNA, based on human placenta 5' cDNA.

FIG. 7 shows an explanatory diagram depicting the 5'-terminal analysis results of human placenta lactogen mRNA, based on human placenta 5' cDNA. As shown in FIG. 7, the nucleotide sequences of 25 clones in total were determined; 20 of the clones were the full-length clone (SEQ ID NOS: 469 to 470) reported in the aforementioned reports. Thus, 80% of the resulting clones corresponded to the full-length clone. Among the remaining 5 clones, 4 of the clones were shorter by one nucleotide (SEQ ID NO: 471); and one of the clones was shorter by 8 nucleotides (SEQ ID NO: 472). The possibility is very high, compared with 5'RACE analysis involving the deletion of several tens of nucleotides in almost all of the resulting clones. Thus, the method according to the present invention was confirmed as a very excellent method for the determination of the nucleotide sequence of the 5'-terminus of mRNA. Additionally, it was confirmed from the results of the invention that a different transcription start (arrow 2) was present in the mRNA, other than the reported transcription start marked with arrow 1.

EXAMPLE 6

Examination of Oligoribonucleotide

The individual oligoribonucleotides shown in Example 4 were examined by using the individual oligoribonucleotides in the reaction system shown in the step 3 of Example 5 to synthesize cDNA finally for subsequent comparison of the amplification degree of human placenta lactogen.

Under the same conditions as in Example 5 except for the modification of the oligonucleotide at the step 3, the reaction was promoted to prepare finally human placenta 5' cDNA.

Using as template human placenta 5' cDNA carrying the sequence from each of the oligoribonucleotides at the 5'-terminus and the primer ASP1 amplifying the placenta lactogen 5' cDNA, synthesizing a primer capable of being annealed to the sequence derived from each of the individual oligoribonucleotides and appropriately diluting the human placenta 5' cDNA, PCR was carried out for the comparison of the amplification degrees with the resulting individual primer sets.

PCR was carried out under the following conditions. 1 μL of template human placenta 5' cDNA in 5-fold seiral dilutions, 2.5 μL of 10 GeneTaq buffer, 2.5 μL of 2.5 mM dNTP mixture solution, 0.5 μL each of ASP1 and each oligoribonucleotide-specific primer (each of 25 μM) and 2.5 U GeneTaq were mixed together to a final reaction volume of 25 μL; one round of 95° C. for 5 minutes and 35 cycles of 94° C. for 30 seconds, 55° C. for 30 seconds and 72° C. for 60 seconds were carried out, followed by a final round of 72° C. for 5 minutes. 5 μL of the resulting PCR product was subjected to 1.2% agarose electrophoresis; and the amplification degree was estimated. The oligoribonucleotide-specific primers used herein are shown below in Table 6. Herein, the sequences of the primers in Table 6 are listed as SQ ID Nos. 11 through 14, below, in the attached sequence listing table.

TABLE 6

| RNA oligo | Primer sequences (5'–3'; name) | |
| --- | --- | --- |
| GG | GCGTTACACAGCGTATGATGCGT | (RC5') |
| AA | GCGTTACACAGCGTATGATGCGT | (RC5') |
| GU | GCGTTACACAGCGTATGATGCGT | (RC5') |
| RC + GU | GTACGCCGTTGCGTTACACAGC | (1RC5') |
| RC + AA | GTACGCCGTTGCGTTACACAGC | (1RC5') |
| RC2 + GU | GCGTTACAAGGTACGCCACAGGT | (1RC2) |
| RC2 + AA | GCGTTACAAGGTACGCCACAGCGT | (1RC2) |
| Vectorette | CGAATCGTAACCGTTCGTACGAG | (vectorette 1) |

Step 1:

The sequences of RNA oligos, namely GG, M and GU, were compared to each other. The results by agarose gel electrophoresis indicate that AA is the most efficient at a ratio of GG:M:GU=1:3:4. It is deduced that the results reflect the reaction efficiency of T4 RNA ligase because the sequences of GG, AA and GU differ only in 3'-terminal sequence. Thus, the 3'-terminus of oligoribonucleotide was prepared with reference to the 3'-terminal sequence of AA or GU.

Step 2:

So as to prepare several primer-binding sites in the cDNA domain derived from each oligoribonucleotide by further elongating the oligoribonucleotide, "RC+GU" and "RC+M" were designed in longer lengths and compared with M and GU. Consequently, the amplification of the PCR product was most sensitively observed with "RC+GU".

Step 3:

From the respect of PCR primer efficiency, other oligoribonucleotides RO1 and RO2 with less CG dinucleotide sequences and small homolog scores were synthesized from the respect of the presence of CpG island at 5'-terminus, together with "RC2+GU" and "RC2+AA" for the comparison of the amplification in different sequences with small homolog scores; additionally, a sequence designed on the basis of the sequence used in the vectorette method reported in Proc. Natl. Acad. Sci. USA, 91 (12): pp.5377–5381 (1994) was synthesized, for comparison. Furthermore, the two types of oligoribonucleotides, namely RO1 and RO2, are composed of the entirety or a part of a series of 10-base sequences (T was modified into U) with no CG dinucleotide sequence (B-19 (Table 4), H-11 (Table 5), E-05 (Table 4), B-33 (Table 2) and C-10 (Table 3)). These sequences are shown in detail as SQ ID Nos. 15 and 16 below in the attached sequence listing table.

Figure 8:
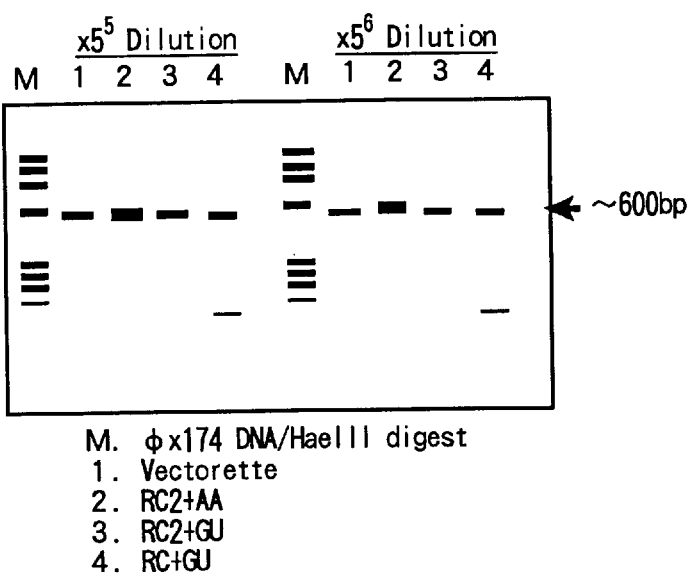
FIG. 8 shows an explanatory diagram depicting the electrophoretic evaluation of PCR 5'-terminal cDNA derived from human placenta lactogen mRNA using the oligoribonucleotide sequence.

FIG. 8 shows an explanatory diagram depicting the examination by PCR and electrophoresis of 5'-terminal cDNA from human placenta lactogen mRNA, as prepared by using various oligoribonucleotide sequences. As shown in the figure, a band about 600-bp was observed sharply in lanes 1, 2, 3 and 4. As indicated in lane 2, however, "RC2+M" the most efficiently amplified the 5'-terminus of placenta lactogen.

EXAMPLE 7

Analysis of Transferrin Receptor 5' cDNA Based on Human Placenta Oligo Capping cDNA In the analysis of the 5' cDNA of human placenta lactogen insofar, the gene with a high expression level such that the expression of human placenta lactogen mRNA amounted to about 3% of all the mRNAs was used as subject. Then, the 5° cDNA of transferrin receptor mRNA was analyzed, of which the expression level is said to belong to medium level.

As a primer amplifying transferrin receptor 5' cDNA, use was made of TFRA3 (5'-GCTTCACATTCTTGCTT TCTGAGG-3') or TFRA4 (5'-GCTTGATGGTGCTGG TGAAGTCTG-3') (McClelland, A., et al. Cell 39: pp.267–274 (1984)). The sequences of these primers TFRA3 and TFRA4 are shown as SQ ID Nos. 17 and 18 in the attached sequence listing table. These were subjected to the following PCR in a final reaction volume of 25 $\mu$L containing 1 $\mu$L of human placenta oligo capping cDNA, 2.5 $\mu$L of 10×GeneTaq buffer, 2.5 $\mu$L of 2.5 mM dNTP mixture solution, 0.5 $\mu$L each of TRFA4 and 1RC2 (each of 25 $\mu$M), and 2.5 U of GeneTaq; PCR was conducted at a round of 95° C. for 5 minutes and 35 cycles of procedures of 94° C. for 30 seconds, 55° C. for 30 seconds and 72° C. for 60 seconds and a final round of 72° C. for 5 minutes.

Figure 9A:
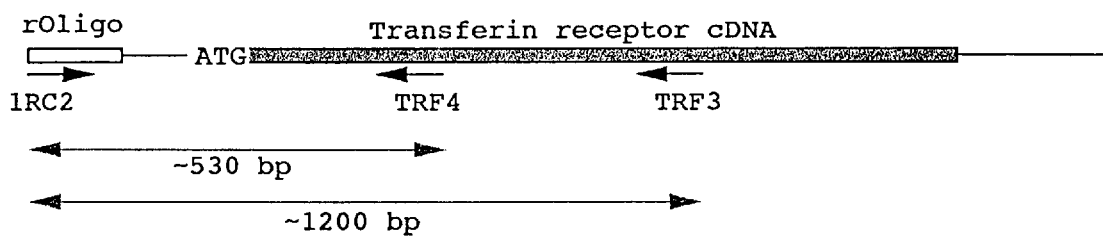
FIG. 9a depicts the approximate sizes of speculative PCR products when two primes are used, namely TFRA3 and TFRA4.
Figure 9B:
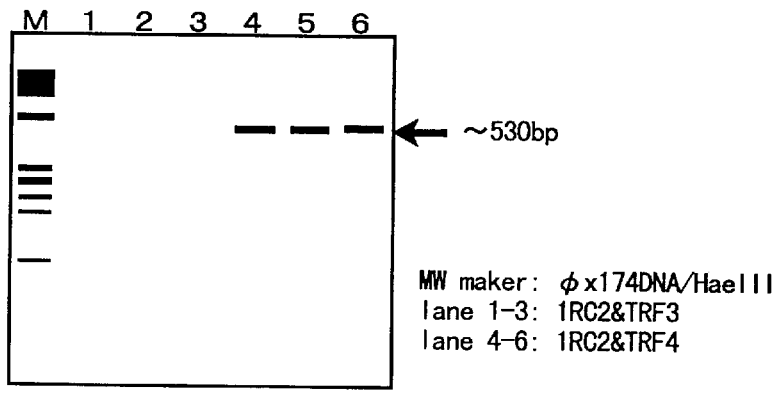
FIG. 9b depicts the schematic electrophoresis results.

FIG. 9 shows an explanatory diagram of the PCR amplification results of the transferrin receptor 5' cDNA, based on the human placenta oligo capping cDNA. In the figure, FIG. 9a depicts the approximate expected sizes of the PCR products when two primes were used, namely TFRA3 and TFRA4; and FIG. 9b schematically shows the electrophoresis results. 5 $\mu$L each of the resulting PCR products was subjected to 1.2% agarose electrophoresis. Consequently, a PCR product was detected at an estimated 530-bp size, when TRFA4 was used. This indicates that the product is derived from the 5'-terminus of human placenta transferrin receptor mRNA. However, no band was observed at an estimated 1200-bp size, when TRFA3 was used, which is indicated to be due to the length of the PCR product recovered by using the primer TRFA3, which is too long. So as to recover such PCR product, importantly, the primer is designed to generate a PCR product of about 300 to 500 bases.

The amplified product blunt ended by using T4 RNA polymerase was subcloned in plasmid pUC19 preliminarily digested with a restriction endonuclease SmaI and treated with dephosphorylation, for the determination of the nucleotide sequence. As reported in Cell, 39: pp.267–274 (1984) and EMBO. J. 6: pp.1287–1293 (1987), it was indicated that the amplified product was the 5'-terminal sequence. Accordingly, it was confirmed that the human placenta oligo capping cDNA of the invention made a fewer copies of mRNA to be effective for the analysis of full-length 5' cDNA of the gene. These results indicate that the inventive method can analyze the 5' cDNA sequence at a very high probability, compared with conventional 5' RACE.

The reason is as follows; according to 5' RACE, PCR is conducted after reverse transcription and adapter attachment, so products recovered with no reverse transcription going up to the transcription start serve as subjects for PCR. In accordance with the present invention, principally, an oligoribonucleotide addition is effected using an enzyme specifically removing the cap structure of RNA, prior to reverse transcription; by PCR using a primer complementary to the oligoribonucleotide, only cDNA containing the transcription start adjacent to the cap structure is a PCR subject; and thus, 5' cDNA can be analyzed at a very high probability (almost 100%).

What is claimed is:

1. A method for synthesizing cDNA including a 5-terminal sequence of a full-length mRNA with a cap structure from a mRNA sample containing the full-length mRNA with the cap structure and a non-full-length mRNA without a cap structure in a mixture, comprising:

(a) removing the phosphate group at the 5'-terminus of the non-full-length mRNA in the mRNA sample;

(b) removing the cap structure at the 5'-terminus of the full-length mRNA in the mRNA sample;

(c) ligating an oligoribonucleotide of a predetermined sequence to the phosphate group at the 5'-terminus of the mRNA generated by step (b) in the sample, said oligoribonucleotide having a sequence prepared by generating a number of oligonucleotide sequences including various combinations of bases in a predetermined number, carrying out a homology search with a predetermined nucleotide sequence data base to determine the occurrence number of a sequence completely matching or differing by one base, and preparing a combination of plural sequences in a low-frequency occurrence group including a sequence at the lowest occurrence number; and (d) subjecting the mRNA ligated with the oligoribonucleotide at the phosphate group at the 5'-terminus to a reverse transcriptase process using as a primer a short-chain oligonucleotide capable of being annealed to an intermediate sequence within the mRNA, to synthesize a first-strand cDNA, wherein said oligoribonucleotide has a sequence selected from the group consisting of:
5'-GUUGCGUUAC-ACAGCGUAUG-AUGCGUAA GG-3' (SEQ ID NO;1),
5'-GUUGCGUUAC-ACAGCGUAUG-AUGCGUAA-3' (SEQ ID NO:2),
5'-GUUGCGUUAC-ACAGCGUAUG-AUGCGU-3' (SEQ ID NO:3),
5'-AAGGUACGCC-GUUGCGUUAC-ACAGCCUA UG-AUGCGU-3' (SEQ ID NO:4),
5'-AAGGUACGCC-GUUGCGUUAC-ACAGCGUA UG-AUGCGUAA-3' (SEQ ID NO:5),
5'-GUUGCGUUAC-AAGGUACGCC-ACAGCGUA UG-AUGCGU-3' (SEQ ID NO:6) and
5'-CUUGCGUUAC-AAGGUACGCC-ACAGCGUA UG-AUGCGUAA-3' (SEQ ID NO: 7).

2. The method according to claim 1, wherein the step (c) comprises ligating an oligoribonucleotide comprising a sequence not contained in the sequence of the mRNA in the mRNA sample, to the phosphate group.

3. The method according to claim 1, wherein the primer used in step (d) comprises a short-chain oligonucleotide of a length of 6 bases or longer.

4. The method according to claim 1, wherein step (b) comprises removing the cap structure at the 5'-terminus of the full-length mRNA in the mRNA sample by contacting the full-length mRNA with a tobacco acid pyrophosphatase purified to a high purity with no contamination of trace amounts of nuclease cleaving the phosphodiester bond comprising RNA and a phosphatase removing 5'-phosphate group freshly generated after cap cleavage.

5. A method for synthesizing cDNA including the 5'-terminal sequence of full-length mRNA with a cap structure from a mRNA sample containing a full-length mRNA with the cap structure and a non-full-length mRNA without a cap structure in a mixture, comprising:

(a) removing the phosphate group at the 5'-terminus of the non-full-length mRNA in the mRNA sample;

(b) removing the cap structure at the 5'-terminus of the full-length mRNA in the mRNA sample by contacting the full-length mRNA with a tobacco acid pyrophosphatase purified to a high purity with no contamination of trace amounts of nuclease cleaving the phosphodiester bond comprising RNA and a phosphatase removing 5'-phosphate group freshly generated after cap cleavage;

(c) ligating an oligoribonucleotide of a predetermined sequence to the phosphate group at the 5'-terminus of mRNA generated by step (b) in the sample, said oligoribonucleotide comprising a sequence prepared by using a combination of plural oligonucleotide sequences in a low occurrence frequency group including an oligonucleotide sequence with the lowest occurrence number among sequences completely matching with or differing by one base from plural 10-mer oligonucleotide sequences of various different base combinations in a predetermined nucleotide data base;

(d) subjecting the mRNA ligated with the oligoribonucleotide at the phosphate group at the 5'-terminus to a reverse transcriptase process using as a primer a short-chain oligonucleotide capable of being annealed to an intermediate sequence within the mRNA, to synthesize a tirst-strand cDNA; and (e) synthesizing a second-strand cDNA based on the resulting first-strand cDNA, wherein said oligoribonucleotide has a sequence selected from the group consisting of:

5'-GUUGCGUUAC-ACAGCGUAUG-AUGCGUAA GG-3' (SEQ ID NO:1),
5'-GUUGCGUUAC-ACAGCGUAUG-AUGCGUAA-3' (SEQ ID NO:2),
5'-GUUGCGUUAC-ACAGCGUAUG-AUGCGU-3' (SEQ ID NO:3),
5'-AAGGUACGCC-GUUGCGUUAC-ACAGCGUA UG-AUGCGU-3' (SEQ ID NO:4),
5'-AAGGUACGCC-GUUGCGUUAC-ACAGCGUA UG-AUGCGUAA-3' (SEQ ID NO:5),
5'-GUUGCGUUAC-AAGGUACGCC-ACAGCGUA UG-AUGCGU-3' (SEQ ID NO:6) and
5'-GUUGCGUAC-AAGGUACGCC-ACAGCGUA UG-AUGCGUAA-3' (SEQ ID NO:7).

6. The method according to claim 5, wherein the tobacco acid pyrophosphatase removes the cap structure at the 5'-terminus and is purified at an extent such that the tobacco acid pyrophosphatase substantially never contains other enzymes cleaving the remaining sites within mRNA.

7. The method according to claim 5, wherein the oligonucleotide has a sequence designed by using a combination of plural oligonucleotide sequences in the low occurrence frequency group including an oligonucleotide sequence with the lowest occurrence frequency, among sequences completely matching with or differing by one base from the plural 10-mer oligonucleotide sequences of various different base combinations in a predetermined nucleotide sequence data base.

8. The method according to claim 7, wherein said oligoribonucleotide has the sequence of:

5'-GUUGCGUUAC-ACAGCGUAUG-AUGCGUAA GG-3' (SEQ ID NO:1).

9. The method according to claim 7, wherein said oligoribonucleotide has the sequence of:

5'-GUUGCGUUAC-ACAGCGUAUG-AUGCGUAA-3' (SEQ ID NO:2).

10. The method according to claim 7, wherein sad oligoribonucleotide has the sequence of:

5'-GUUGCGUUAC-ACAGCGUAUG-AUGCGU-3' (SEQ ID NO:3).

11. The method according to claim 7, wherein said oligoribonucleotide has the sequence of:

5'-AAGGUACGCC-GUUGCGUUAC-ACAGCGUA UG-AUGCGU-3'(SEQ ID NO:4).

12. The method according to claim 7, wherein said oligoribonucleotide has the sequence of:

5'-AAGGUACGCC-GUUGCGUUAC-ACAGCGUA UG-AUGCGUAA-3' (SEQ ID NO:5).

13. The method according to claim 6, wherein said oligoribonucleotide has the sequence of:

5'-GUUGCGUUAC-AAGGUACGCC-ACAGCGUA UG-AUGCGU-3' (SEQ ID NO:6).

14. The method according to claim 7, wherein said oligoribonucleotide has the sequence of:

5'-GUUGCGUUAC-AAGGUACGCC-ACAGCGUA UG-AUGCGUAA-3' (SEQ ID NO:7).

15. The method according to claim 1, wherein said oligoribonucleotide has the sequence of:

5'-GUUGCGUUAC-ACAGCGUAUG-AUGCGUAA GG-3' (SEQ ID NO:1).

16. The method according to claim 1, wherein said oligoribonucleotide has the sequence of:

5'-GUUGCGUUAC-ACAGCGUAUG-AUGCGUAA-3' (SEQ ID NO:2).

17. The method according to claim 1, wherein said oligoribonucleotide has the sequence of:

5' -GUUCGCGUUAC-ACAGCGUAUG-AUGCGU-3' (SEQ ID NO:3).

18. The method according to claim 1, wherein said oligoribonucleotide has the sequence of:

5'-AAGGUACGCC-GUUGCGUUAC-ACAGCGUA UG-AUGCGU-3' (SEQ ID NO:4).

19. The method according to claim 1, wherein said oligoribonucleotide has the sequence of:

5'-AAGGUACGCC-GWGCGUUAC-ACAGCGUAUG-AUGCGUAA-3' (SEQ ID NO:5).

20. The method according to claim 1, wherein said oligoribonucleotide has the sequence of:

5'-GUUGCGUUAC-AAGGUACGCC-ACAGCGUA UG-AUGCGU-3' (SEQ ID NO:6).

21. The method according to claim 1, wherein said oligoribonucleotide has the sequence of:

5'-GUUGCGUUAC-AAGGUACGCC-ACAGCGUA UG-AUGCGUAA-3' (SEQ ID NO:7).

* * * * *